US010006026B2

(12) United States Patent
Streicher et al.

(10) Patent No.: US 10,006,026 B2
(45) Date of Patent: Jun. 26, 2018

(54) RECOMBINANT POLYPEPTIDE PRODUCTION

(71) Applicant: MedImmune, LLC, Gaithersburg, MD (US)

(72) Inventors: Katie Streicher, Gaithersburg, MD (US); Jonathan Jacobs, Gaithersburg, MD (US); Robert W. Georgantas, III, Gaithersburg, MD (US); Lydia Greenlees, Gaithersburg, MD (US); Koustubh Ranade, Gaithersburg, MD (US); Michael Bowen, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days. days.

(21) Appl. No.: 14/775,233

(22) PCT Filed: Mar. 12, 2014

(86) PCT No.: PCT/US2014/024512
§ 371 (c)(1),
(2) Date: Sep. 11, 2015

(87) PCT Pub. No.: WO2014/159633
PCT Pub. Date: Oct. 2, 2014

(65) Prior Publication Data
US 2016/0024502 A1 Jan. 28, 2016

Related U.S. Application Data

(60) Provisional application No. 61/782,180, filed on Mar. 14, 2013.

(51) Int. Cl.
*C12N 15/113* (2010.01)
*C12P 21/02* (2006.01)
*C07K 14/705* (2006.01)
*C07K 16/00* (2006.01)
*C07K 16/42* (2006.01)
*C12N 9/00* (2006.01)

(52) U.S. Cl.
CPC .......... *C12N 15/113* (2013.01); *C07K 14/705* (2013.01); *C07K 16/00* (2013.01); *C07K 16/4208* (2013.01); *C12N 9/00* (2013.01); *C12P 21/02* (2013.01); *C07K 2317/14* (2013.01); *C07K 2317/21* (2013.01); *C07K 2317/22* (2013.01); *C07K 2317/24* (2013.01); *C07K 2317/31* (2013.01); *C07K 2317/40* (2013.01); *C07K 2317/565* (2013.01); *C07K 2317/622* (2013.01); *C12N 2310/113* (2013.01); *C12N 2330/50* (2013.01); *C12N 2799/027* (2013.01); *C12Q 2600/178* (2013.01)

(58) Field of Classification Search
CPC ... A61K 48/00; C12N 15/113; C12N 2310/11
See application file for complete search history.

(56) References Cited

U.S. PATENT DOCUMENTS

| 2009/0035862 A1 | 2/2009 | Calos |
| 2010/0190258 A1 | 7/2010 | Gammell |
| 2010/0226884 A1 | 9/2010 | Chang et al. |
| 2010/0267573 A1 | 10/2010 | Keene et al. |
| 2011/0098346 A1 | 4/2011 | Wang et al. |
| 2011/0189137 A1 | 8/2011 | Rana |
| 2011/0224286 A1 | 9/2011 | Yu et al. |
| 2012/0230959 A1 | 9/2012 | Abbot et al. |

FOREIGN PATENT DOCUMENTS

| WO | 2008015662 A1 | 2/2008 |
| WO | 2010129919 A1 | 11/2010 |

OTHER PUBLICATIONS

Ambros, V. (2001) microRNAs: tiny regulators with great potential. Cell 107(7):823-826.
Barron et al. (2011) "Engineering CHO cell growth and recombinant polypeptide productivity by over expression of miR-7," Journal of Biotechnology 151(2):204-11.
De Vito et al., (2011) Let-7a Is Direct EWS-FLI-1 Target Implicated in Ewing's Sarcoma Development. PLoS ONE, 6(8):1-11.
Druz et al., "A novel microRNA mmu-mir-466h affects apoptosis regulation in mammalian cells", Biotechnol Bioeng, Jul. 2011, vol. 108(7): 1651-1661.
Gammell et al. (2007) "Initial identification of low temperature and culture stage induction of miRNA expression in suspension CHO-K1 cells." Journal of Biotechnology 130:213-218.
Hackl et al. (2011) "Next-generation sequencing of the Chinese hamster ovary microRNA transcriptome: Identification, annotation and profiling of microRNAs as targets for cellular engineering." Journal of Biotechnology 153(1-2):62-75.
He et al. (2009) Let-7a elevates p21WAF1 levels by targeting of NIRF and suppresses the growth of A549 lung cancer cells. FEBS Letters 583:3501-3507.
International Search Report corresponding to PCT/US14/24512 dated Jul. 22, 2014.
Johnson et al., (2005) RAS Is Regulated by the let-7 MicroRNA Family. Cell 120:635-647.
Johnson et al., (2007) The let-7 MicroRNA Represses Cell Proliferation Pathways in Human Cells. Cancer Res 67:7713-7722.
Lin et al., (2011) Follicular dendritic cell-induced microRNA-mediated upregulation of PRDM1 and downregulation of BCL-6 in non-Hodgkin's B-cell lymphomas. Leukemia 25(1):145-152.
Lu et al., (2007) Hypermethylation of let-7a-3 in Epithelial Ovarian Cancer Is Associated with Low Insulin-Like Growth Factor-II Expression and Favorable Prognosis. Cancer Res 67(21):10117-10122.

(Continued)

*Primary Examiner* — Amy H Bowman

(57) ABSTRACT

Disclosed herein is a method for producing a recombinant polypeptide in a mammalian cell culture in which the mammalian cells have a modified microRNA activity level. In one embodiment, a microRNA activity level is increased. In another embodiment, a microRNA activity level is decreased. In a more particular embodiment, the mammalian cells have a reduced miRNA-let-7a activity level.

20 Claims, 13 Drawing Sheets

(56) References Cited

OTHER PUBLICATIONS

Mathonnet et al., (2007) MicroRNA Inhibition of Translation Initiation in Vitro by Targeting the Cap-Binding Complex eIF4F. Science 317(5845):1764-1767.

Meleady et al., "Sustained productivity in recombinant Chinese Hamster Ovary (CHO) cell lines: proteome analysis of the molecular basis for a process-related phenotype", BMC Biotechnol., Jul. 24, 2011, vol. 11:78, pp. 1-11.

Meng et al., (2007) The MicroRNA let-7a Modulates Interleukin-6-dependent STAT-3 Survival Signaling in Malignant Human Cholangiocytes. Journal of Biological Chemistry 282(11):8256-8264.

Muller et al. (2008) "MicroRNAs as targets for engineering of CHO cell factories." Trends in Biotechnology 26(7):359-365.

Sampson et al. (2007) "MicroRNA Let-7a down-regulates MYC and reverts MYC-Induced Growth in Burkitt Lymphoma Cells." Cancer Res 67(20):9762-9770.

Wang et al., (2012) NIRF is frequently upregulated in colorectal cancer and its oncogenicity can be suppressed by let-7a microRNA. Cancer Letters 314:223-231.

Yang et al., (2011) Low-level expression of let-7a in gastric cancer and its involvement in tumorigenesis by targeting RAB40C. Carcinogenesis 32(5):713-722.

Khodayari, N. et al., "EphrinA1 inhibits Malignant Mesothelioma Tumor Growth Via let-7 microRNA-Mediated Repression of the RAS Oncogene", Cancer Gene Therapy, Aug. 26, 2011, vol. 18, pp. 806-816.

Roush S et al: "The let-7 family of microRNAs", Trends in Cell Biology, vol. 18, No. 10, Sep. 4, 2008, pp. 505-516.

Noelia Sanchez: "miRNAs as tools to improve CHO cell bioprocess phenotypes", Ph. D. thesis, Jan. 2013, pp. i-xi, 1-474, XP055303658, Dublin, Ireland Retrieved from the Internet: URL:http://doras.dcu.ie/17716/1/Final_bound_thesis_NSanchez.pdf [retrieved on Sep. 19, 2016].

Druz, Aliaksandr et al: "Stable inhibition of mmu-miR-466h-5p improves apoptosis resistance and protein production in CHO cells", Metabolic Engineering, vol. 16, Jan. 29, 2013, pp. 87-94.

Tsang, Wing Pui et al: "Let-7a microRNA suppresses therapeutics-induced cancer cell death by targeting caspase-3", Apoptosis; vol. 13, No. 10, Aug. 29, 2008, pp. 1215-1222.

Robertson Barbara et al: "Specificity and functionality of microRNA inhibitors", Silence, vol. 1, No. 1, Apr. 1, 2010, p. 1-11

Barron, Niall et al: "MicroRNAs: tiny targets for engineering CHO cell phenotypes?", Biotechnology Letters. Springer Netherlands. Dordrecht. vol. 1 • 33. No. 1, Sep. 25, 2010 (Sep. 25, 2010). pp. 11-21.

Hernandez Bort, Juan A. et al: "Dynamic mRNA and miRNA profiling of CHO-K1 suspension cell cultures" Biotechnology Journal, vol. 7. No. 4. Aug. 5, 2011 (Aug. 5, 2011). pp. 500-515.

Jadhav, Vaibhav et al: "A screening method to assess biological effects of microRNA overexpression in Chinese hamster ovary cells", Biotechnology and Bioengineering. vol. 1 • 109. No. 6, Mar. 22, 2012 (Mar. 22, 2012). pp. 1376-1385.

Jadhav, Vaibhav et al: CHO mi croRNA engineering is growing up: Recent successes and future challenges:, Biotechnology Advances, vol. 31. No. 8. Aug. 2, 2013 (Aug. 2, 2013), pp. 1501-1513.

Greenlees, Lydia et al: "Inhibition of microRNA-let-7a Increases the Specific Productivity of Antibody-Producing CHO Cell Lines", Genomics and Applied Biology, vol. 5. No. 1. Jul. 26, 2014 (Jul. 26, 2014). pp. 1-15.

Clarke, Colin et al: "Large scale microarray profiling and coexpression network analysis of CHO cells identifies transcriptional modules associated with growth and productivity," Journal of Biotechnology, vol. 155,Issue 3, Sep. 20, 2011, pp. 350-359.

Preliminary Report on Patentability for corresponding PCT/US14/24512 dated Sep. 24, 2015.

Supplementary Search Report corresponding to EP 14776.495.5 dated Apr. 10, 2016.

Search Opinion for corresponding EP 14776.495.5 dated Apr. 27, 2016.

Search Strategy for corresponding EP 14776.495.5 dated Oct. 12, 2016.

Hutvagner et al., (2004), "Sequence-Specific Inhibition of Small RNA function", PLoS Biol. 2(4):0465-0475.

| mAb-Producing Cell Line | Relative Production Level (compared to line #1) | % Increase in Qp over control |
|---|---|---|
| 1 | 1 | 68% |
| 2 | 1.6 | 50% |

| | RAS Expression | | |
|---|---|---|---|
| | Parent | Control | Anti-miR-let7a |
| Normalized to GAPDH | 0.0526 | 0.0500 | 0.0680 |
| Fold Increase Compared to Control | 1.05 | 1.00 | |

B.

A.

C.

B.

SEQUENCE LISTING

<160> NUMBER OF SEQ ID NOS: 12

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uacccuguag auccgaauuu gug                                              23

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uagcuuauca gacugauguu ga                                               22

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ugagguagua gguuguauag u                                                21

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uagcagcacg uaaauauugg cg                                               22

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uacaguacug ugauaacuga a                                                21

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guccaguuuu cccaggaauc ccu                                              23

```
<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugagaugaag cacuguagcu c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actatacaac ctactacctc a                                              21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgccaatatt tacgtgctgc ta                                             22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttcagttatc acagtactgt a                                              21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agggattcct gggaaaactg gac                                            23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gagctacagt gcttcatctc a                                              21
```

RECOMBINANT POLYPEPTIDE PRODUCTION

CROSS-REFERENCE TO RELATED APPLICATIONS

This application is a U.S. National Stage application of International Application No. PCT/US2014/024512, filed on Mar. 12, 2014, said International Application No. PCT/US2014/024512 claims benefit under 35 U.S.C. § 119(e) of the U.S. Provisional Application No. 61/782,180, filed Mar. 14, 2013. Each of the above listed applications is incorporated by reference herein in its entirety for all purposes.

REFERENCE TO THE SEQUENCE LISTING

This application incorporates by reference a Sequence Listing submitted with this application as text file entitled miRNA-100US1_Seq, created on Aug. 18, 2015, and having a size of 4.00 kilobytes.

1. FIELD OF THE INVENTION

The invention relates to production of recombinant polypeptides. More specifically, the invention relates to the regulation of miRNA to increase the productivity of recombinant polypeptide producing cell lines, e.g., by increasing or decreasing levels of one or more miRNAs.

2. BACKGROUND

Cultivated mammalian cells are often used for production of recombinant polypeptides. Mammalian cell culture offers many advantages over non-mammalian systems, including, for example, proper protein folding, assembly and post-translational modification. However, there still exist challenges to improving productivity of large-scale mammalian cultures including, for example, challenges relating to growth level, cellular stress, and translation rate. In many industrial cell culture processes, cells are cultured at a high density in a large-scale bioreactor as a suspension and often the cells are proliferated beyond their optimal growth conditions. Under these conditions, apoptosis may be triggered, and as a result, cell viability and productivity may decrease. Consequently, many production optimization strategies rely on prevention of apoptosis and altering cellular metabolism by enhancing media formulations and growth conditions. Recent research suggests that cell productivity can be increased by altering global gene expression patterns of key molecules, such as transcription factors, that regulate multiple critical cellular pathways.

MicroRNAs (miRNAs) are small non-coding RNA molecules of about 22 nucleotides that are found in plants and animals and are key transcriptional and post-transcriptional regulators of gene expression. miRNAs function by base-pairing with complementary sequences within mRNA molecules, often resulting in gene silencing and are involved in diverse biological pathways in animals and plants including regulatory functions relating to cell growth, development and differentiation. miRNAs play a key role in maintaining cellular homeostasis and regulating important cellular pathways, such as growth and apoptosis. Inappropriate miRNA expression has been associated with a number of diseases, including cancer, where they may contribute to pathogenesis by altering numerous proteins and pathways simultaneously.

The ability for a change in a single miRNA to affect multiple physiological processes indicates that modifying miRNA expression in production cell culture may extend the productive cell growth phase, generate higher antibody titers and increase productivity (Sampson et al. (2007) "MicroRNA Let-7a down-regulates MYC and reverts MYC-induced growth in Burkitt Lymphoma cells." Cancer Res 67(20):9762-9770; Muller et al. (2008) "MicroRNAs as targets for engineering of CHO cell factories." Trends in Biotechnology 26(7):359-365; and Barron et al. (2011) "Engineering CHO cell growth and recombinant polypeptide productivity by over expression of miR-7." Journal of Biotechnology 151(2):204-11). Accordingly, investigators have begun to examine the role of microRNAs in mammalian cell cultures, primarily through analysis of alterations in endogenous miRNAs that occur throughout production culture (Muller et al. (2008) "MicroRNAs as targets for engineering of CHO cell factories." Trends in Biotechnology 26(7):359-365; Barron et al. (2011) "Engineering CHO cell growth and recombinant polypeptide productivity by over expression of miR-7." Journal of Biotechnology 151(2):204-11; Gammell et al. (2007) "Initial identification of low temperature and culture stage induction of miRNA expression in suspension CHO-K1 cells." Journal of Biotechnology 130:213-218; and Hackl et al. (2010) "Next-generation sequencing of the Chinese hamster ovary microRNA transcriptome: Identification, annotation and profiling of microRNAs as targets for cellular engineering." Journal of Biotechnology 153(1-2):62-75). A small number of studies have also explored the effect of ectopically expressed miRs or anti-miRs on CHO cells (Barron et al., 2011; Meleady et al., 2011; Druz et al., 2011). However, more careful characterization of the effects of altered miRNA in CHO cells is necessary before this technology can be implemented routinely to increase production of therapeutic biologics.

3. SUMMARY

Disclosed herein is a method of producing a recombinant polypeptide in a mammalian cell culture in which the mammalian cells have reduced miRNA-let-7a activity. In one embodiment, miRNA-let-7a activity is reduced by a microRNA inhibitor. In one embodiment, the microRNA inhibitor includes an antisense oligonucleotide inhibitor of miRNA-let-7a. In another embodiment, the mammalian cell culture includes mammalian cells that are transfected with a synthetic antisense oligonucleotide inhibitor of miRNA-let-7a. In one embodiment, the oligonucleotide inhibitor is chemically modified to improve nuclease resistance, to increase resistance to miRNA-directed cleavage by RISC and/or to increase binding affinity. In one embodiment, the mammalian cell culture includes mammalian cells that are transfected with an expression vector encoding the antisense oligonucleotide inhibitor of miRNA-let-7a. The mammalian cell culture can be stably or transiently transfected with the antisense oligonucleotide inhibitor of miRNA-let-7a. In another embodiment, the mammalian cells include miRNA-let-7a genetic knockouts.

Suitable mammalian cells include but are not limited to, for example, Chinese hamster ovary (CHO) cells, mouse myeloma (NS0), human embryonic kidney (HEK 293 and derivatives such as 293T, 293H), baby hamster kidney (BHK) cells, Vero cells, HeLa cells, Madin-Darby Canine Kidney (MDCK) cells, CV1 monkey kidney cells, 3T3 cells, myeloma cell lines, PC12, WI38 cells, COS-7 lines of monkey kidney fibroblasts, and C127.

Suitable recombinant polypeptides include antibodies or binding fragments thereof and non-antibody proteins. In one embodiment, the antibody or binding fragment thereof is selected from multispecific antibodies, fully human antibodies, humanized antibodies, camelised antibodies, chimeric antibodies, CDR-grafted antibodies, single-chain Fvs (scFv), disulfide-linked Fvs (sdFv), Fab fragments, F(ab') fragments, and anti-idiotypic (anti-Id) antibodies. In one embodiment, the antibody or binding fragment thereof includes an isotype selected from IgG, IgE, IgM, IgD, IgA and IgY. In another embodiment, the antibody includes an isotype selected from IgG1, IgG2, IgG3 and IgG4.

In another embodiment, the recombinant polypeptide includes a non-antibody protein. In one embodiment, the recombinant polypeptide includes a fusion protein. In another embodiment, the recombinant polypeptide includes a receptor. In one embodiment, the recombinant polypeptide includes a ligand of a cell surface protein. In another embodiment, the cell surface protein is a receptor. In another embodiment, the recombinant polypeptide includes a secreted protein. In another embodiment, the recombinant polypeptide includes an enzyme. In another embodiment, the recombinant polypeptide includes a scaffold mimetic.

In one embodiment, the cell culture has a specific productivity that is increased at least about 25% compared to a control cell culture that does not have reduced miRNA-let-7a activity. In one embodiment, the cell culture has a maximum productivity determined at peak viable cell density (VCD) that is increased at least about 25% when compared to a control cell culture that does not have reduced miRNA-let-7a activity. In one embodiment, the cell culture has increased specific productivity, where the titer of antibody per viable cell is increased in the cell culture as compared to a control cell culture that does not have reduced miRNA-let-7a activity.

In one embodiment, expression of at least one mediator of apoptosis, protein translation or cellular metabolism is increased in the mammalian cell culture when compared to a control cell culture that does not have reduced miRNA-let-7a activity. In one embodiment, expression of at least one target of miRNA-let-7a selected from HMGA2, MYC, NF2, NIRF, RAB40C, and eIF4a is increased in the cell culture when compared to a control cell culture that does not have reduced miRNA-let-7a activity.

In one embodiment, the mammalian cells have increased activity of a second microRNA selected from miR-10a, miR-21, and combinations thereof as compared to a control cell culture. In one embodiment, the mammalian cells are transfected with an expression vector capable of expressing miR-10a, miR-21, or a combination thereof. In one embodiment, the mammalian cells have decreased activity of a second microRNA selected from miR-16, miR-101, miR-145, and combinations thereof. In one embodiment, activity of the second microRNA is reduced by a second microRNA inhibitor. In one embodiment, the second microRNA inhibitor includes an antisense oligonucleotide inhibitor. In one embodiment, the mammalian cell culture includes mammalian cells that are transfected with the second antisense oligonucleotide inhibitor. In one embodiment, the second oligonucleotide inhibitor is chemically modified to improve nuclease resistance, to increase resistance to miRNA-directed cleavage by RISC and/or to increase binding affinity. In one embodiment, the mammalian cell culture includes mammalian cells that are transfected with an expression vector encoding the second antisense oligonucleotide inhibitor.

Also disclosed are mammalian cell lines configured to express a recombinant polypeptide, wherein the mammalian cell line has reduced miRNA-let-7a activity; expression systems that include one or more vectors encoding an antisense microRNA inhibitor of miRNA-let-7a and a nucleotide sequence encoding a recombinant protein; cell culture media that include an antisense inhibitor of miRNA-let-7a.; and recombinant polypeptides produced from a mammalian cell culture including mammalian cells transfected with an antisense microRNA inhibitor of miRNA-let-7a.

4. BRIEF DESCRIPTION OF THE DRAWINGS

FIG. 7 is a table showing % increase in cumulative Qp relative to control in two cell lines producing recombinant mAb.

Figure 9:
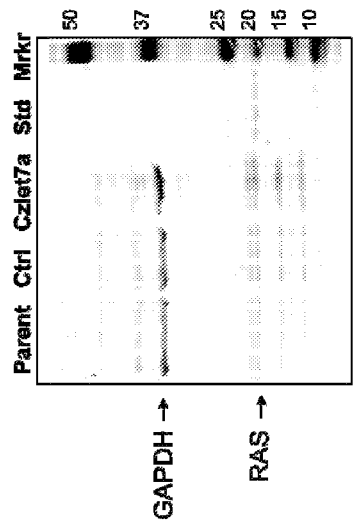

FIGS. 9 A and B. (A) shows densitometric measurements were used to calculate the % change in the RAS/GAPDH ratio following inhibition of miR-let-7a compared to control. (B) is a Western blot showing protein levels of RAS and the loading control GAPDH in parental, control, and anti-miR-let-7a cell lines.

Figure 10:
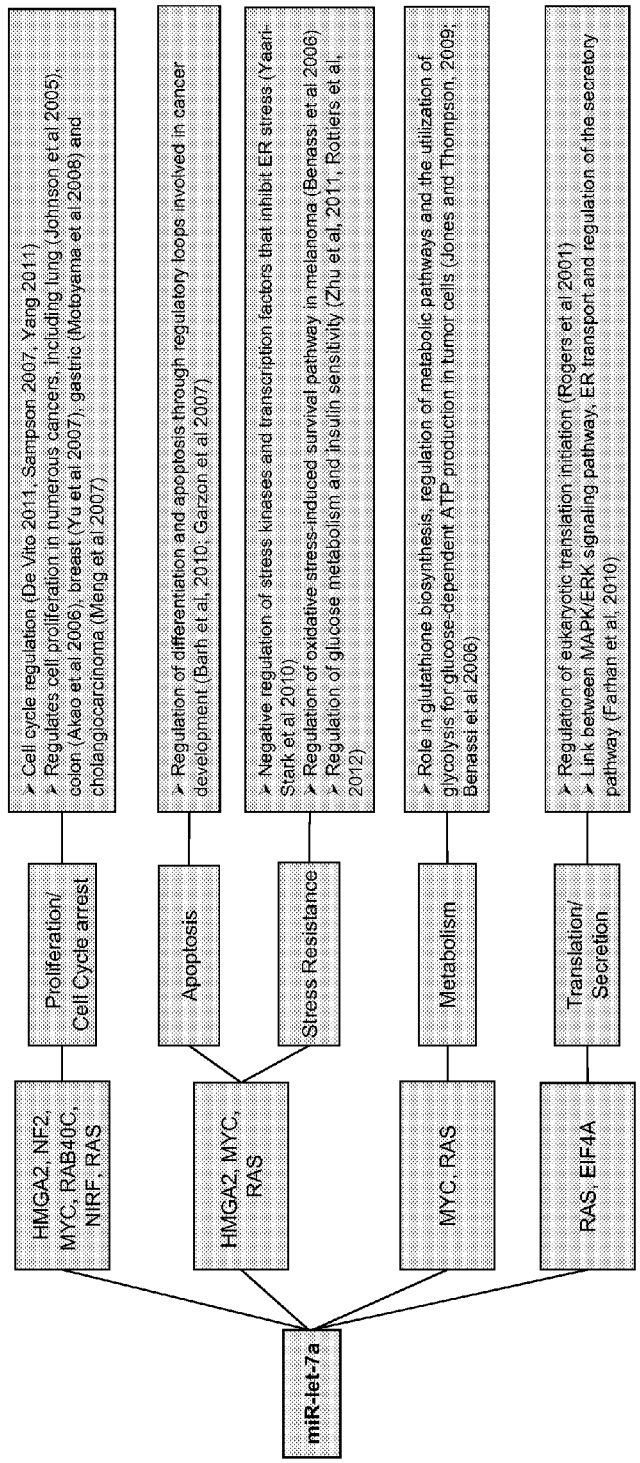

FIG. 10 is a flow chart showing target genes involved in multiple cellular pathways including proliferation/cell cycle, apoptosis, stress resistance, metabolism and transcription/translation that were altered due to modulation of miR-let-7a in antibody-producing cell lines.

Figure 11:
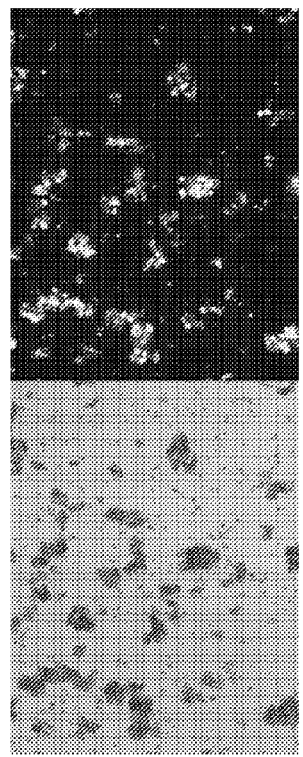
Figure 11:
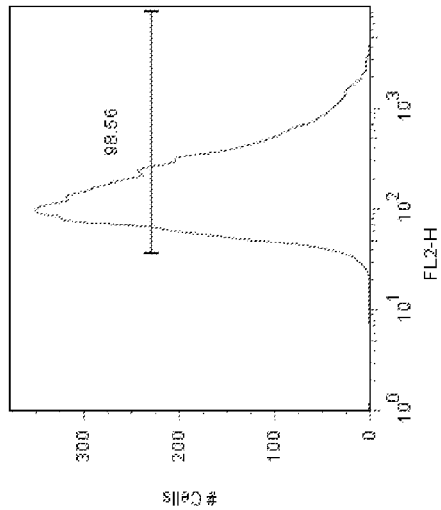
Figure 11:
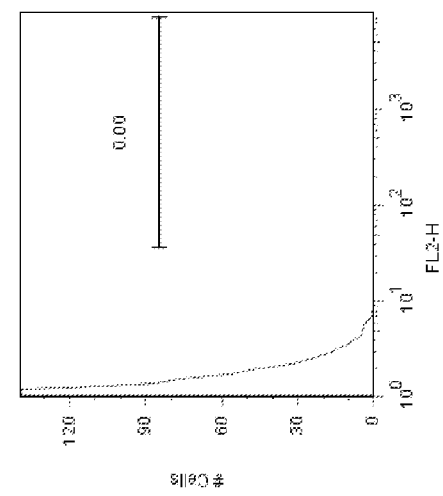

FIGS. 11 A-C. (A) is a representative photomicrograph of CHO cells transduced with a lentivector expressing an anti-miR and GFP indicating transduction efficiencies approach 100%. (B) and (C) are representative FACS histograms showing a 2 log shift in fluorescence values (RFP) in CHO cells transduced with lentivirus compared to parental cells.

Figure 12:
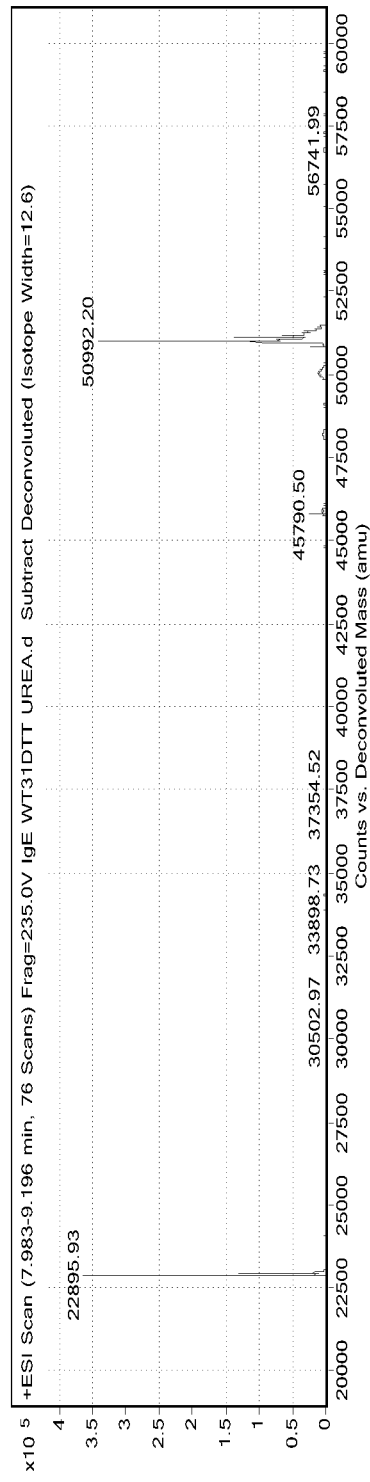
Figure 12:
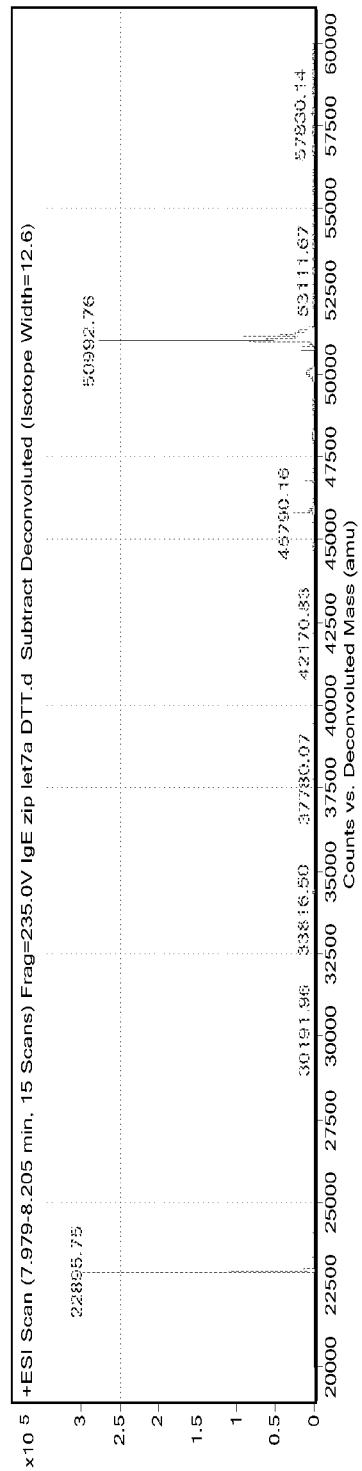

FIGS. 12 A and B are representative deconvoluted ESI mass spectra of a representative monoclonal antibody from parental line—reducing HC and LC mass. LC 22895.9263 matching LC and HC (G0F) 50992.2014 matching G0F; 51154.2639 matching G1F; and 51316.1579 matching G2F; and (B) antibody from anti-miR-let-7a modified line reducing HC and LC mass. LC 22895.7493 matching LC and HC (G0F) 50992.7636 matching G0F and 51154.3954 matching G1F.

5. DETAILED DESCRIPTION

A. Overview

Embodiments of the invention described herein relate to methods for producing recombinant polypeptides in mammalian cell culture. In one embodiment, the method includes culturing mammalian cells in the presence of microRNA to increase cell line productivity. In a more particular embodiment, mammalian cell lines can be engineered to alter microRNA activity to increase recombinant polypeptide productivity.

B. Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection, viral transduction). Enzymatic reactions and purification techniques are performed according to manufacturer's specifications or as commonly accomplished in the art or as described herein. The techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation and delivery e.g., for the treatment of patients.

As used in accordance with the present disclosure, the following terms, unless otherwise indicated, shall be understood to have the following meanings:

As used herein, the term "about" is used to modify, for example, the quantity of an ingredient in a composition, concentration, volume, process temperature, process time, yield, flow rate, pressure, and ranges thereof, employed in describing the invention. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and other similar considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include such equivalents.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', $F(ab')_2$ single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)-Fc fusions and scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "control sequence" as used herein refers to polynucleotide sequences that effect or affect the expression and processing of coding sequences to which they are connected. The nature of such control sequences may differ depending upon the host organism. In eukaryotes, control sequences may include promoters, enhancers, introns, transcription termination sequences, polyadenylation signal sequences, and 5' and 3' untranslated (UTR) regions. The term "control sequences" as used herein includes all components whose presence is necessary for expression and processing, and can also include additional components whose presence is not necessary, but still advantageous, for example, leader sequences.

The term "gene" is used broadly to refer to any nucleic acid associated with a biological function. Thus, the term "gene" includes coding sequences and/or regulatory sequences required for expression. The term "gene" can also apply to a specific genomic sequence, as well as to a cDNA or an mRNA encoded by that genomic sequence.

The term "heterologous gene" refers to a gene encoding a biological material that is not in its natural environment (i.e., has been altered by the hand of man). For example, a heterologous gene can include a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous genes in that the heterologous gene sequences may be joined to regulatory elements, such as promoters, that are not found naturally associated with the gene or are associated with portions of the chromosome not found in nature.

The term "host cell" means a cell which can or has taken up a nucleic acid, such as a vector, and supports the replication and/or expression of the nucleic acid, and optionally production of one or more encoded products. In one embodiment, the term "host cell" refers to an eukaryotic cell, such as a mammalian cell in a cell culture. In a more particular embodiment, the host cells include Chinese hamster ovary (CHO) cells, human embryonic kidney (HEK 293 and derivatives such as 293T, 293H) cells, Vero cells, baby hamster kidney (BHK) cells, HeLa cells, CV1 monkey kidney cells, Madin-Darby Canine Kidney (MDCK) cells, 3T3 cells, myeloma cell lines, COS cells (e.g., COS1 and COS7) PC12, WI38 cells. The term host cell also encompasses combinations or mixtures of cells including, e.g., mixed cultures of different cell types or cell lines.

The term "introduced" when referring to a heterologous or isolated nucleic acid refers to the incorporation of a nucleic acid into a eukaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." A variety of methods are known and can be employed to introduce nucleic acids into mammalian cells.

The term "isolated" when used herein in connection with a biological material, such as a nucleic acid or a protein, refers to a biological material that has been isolated from its naturally occurring environment. "Isolated" polynucleotide can refer to genomic, cDNA, or a synthetic polynucleotide. Isolated polynucleotides may be operably linked to another polynucleotide to which it is not linked in nature. The term "isolated," when used in connection with a protein, refers to a protein that has been isolated from its naturally occurring environment. Isolated proteins may be derived from genomic DNA, cDNA, recombinant DNA, recombinant RNA, or synthetic origin or some combination thereof.

The term "mAb" refers to a monoclonal antibody.

The term "naturally-occurring" refers to a biological material that is present in an organism, for example, a polypeptide, polynucleotide or microRNA sequence, wherein the biological material has not been intentionally modified by man. The term "exogenous" refers to a biological material that originates from outside of an organism or that is present in an organism due to an intentional modification by man, including, for example, modification of the organism to express the biological material.

The terms "nucleic acid," "oligonucleotide" and "polynucleotide" refer to single-stranded or double-stranded deoxyribonucleotide or ribonucleotide polymers, or chimeras or analogues thereof. Unless otherwise indicated, a nucleic acid sequence encompasses complementary sequences, in addition to the sequence explicitly indicated. Oligonucleotides are a polynucleotide subset generally having a length of up to about 200 bases, for example, between about 10 to about 100 bases.

The term "operably linked" as used herein refers to positions of components that are in a relationship permitting them to function in their intended manner. For example, a control sequence "operably linked" to a coding sequence is connected in such a way that expression of the coding sequence is achieved under conditions compatible with the control sequences.

The terms "peptide," "polypeptide" and "protein" are used interchangeably throughout and refer to a molecule comprising two or more amino acid residues joined to each other by peptide bonds. The terms "peptide," "polypeptide" and "protein" can refer to antibody and non-antibody proteins. Non-antibody proteins include, but are not limited to, proteins such as enzymes, receptors, ligands of a cell surface protein, secreted proteins and fusion proteins or fragments thereof. Non-antibody proteins tend to have a lower molecular weight than antibody proteins. The polypeptide may or may not be glycosylated. The protein may or may not be fused to another protein. Peptides, polypeptides and proteins can also include modifications such as, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies and chimeric or fusion proteins.

A "promoter" or "promoter sequence" is a DNA regulatory region capable of initiating transcription of a nucleic acid sequence to which it is operably linked, when appropriate transcription-related enzymes, e.g., RNA polymerase, are present under conditions, e.g., culture or physiological conditions, whereby the enzymes are functional. A promoter can be present upstream or downstream from the nucleic acid sequence whose transcription it initiates. A transcription initiation site is typically found within or adjacent to the promoter sequence as well as protein binding domains (consensus sequences) that promote, regulate, enhance, or are otherwise responsible for the binding of RNA polymerase.

The term "recombinant" refers to a biological material, for example, a nucleic acid or protein, that has been artificially or synthetically (i.e., non-naturally) altered by human intervention.

As used herein, "substantially pure" refers to a biological material that is the predominant species present (e.g., on a molar basis it is more abundant than any other individual species in the composition). In one embodiment, a substantially purified fraction is a composition wherein the biological material includes at least about 50% (on a molar basis) of all macromolecular species present. Generally, a substantially pure composition will include more than about 80% of all macromolecular species present in the composition, or more than about 85%, more than about 90%, more than about 95%, or more than about 99%. In one embodiment, the biological material is purified to essential homogeneity (contaminant species cannot be detected in the composition by conventional detection methods) and the composition includes essentially a single macromolecular species.

The term "transfection" refers to the introduction of foreign DNA into cells. The terms "transfect" and "transform" (and grammatical equivalents, such as "transfected" and "transformed") are used interchangeably. The term "stable transfection" or "stably transfected" refers to the introduction and integration of foreign DNA into the genome of the transfected cell. The term "transient transfection" or "transiently transfected" refers to the introduction of foreign DNA into a cell where the foreign DNA does not integrate into the genome of the transfected cell. In transient transfection, the foreign DNA can persist in the nucleus of the transfected cell for several days, during which time the foreign DNA is subject to the regulatory controls that govern the expression of endogenous genes in the chromosomes.

The term "vector" refers to a nucleic acid, e.g., a plasmid, viral vector, recombinant nucleic acid or cDNA that can be used to introduce heterologous nucleic acid sequences into a cell. An "expression vector" is a vector, such as a plasmid, which is capable of promoting expression, e.g., transcription, of a nucleic acid incorporated therein. Typically, the nucleic acid to be expressed is "operably linked" to a promoter and/or enhancer, and is subject to transcription regulatory control by the promoter and/or enhancer.

C. Micro RNAs

MicroRNAs (miRs, miRNAs) are a class of naturally occurring, small non-coding RNAs between about 17 and about 27 nucleotides in length, between about 19 and about 25 nucleotides in length, or between about 21 and about 23 nucleotides in length, often 22 nucleotides in length that are expressed in mammalian cells. miRNAs can downregulate gene expression in mammals by binding to imperfectly complementary sequences in the 3'untranslated region (UTR) of target messenger RNA (mRNA) and inhibiting translation of the mRNA, for example, by preventing ribosome binding, translational repression, deadenylation or by inducing or accelerating mRNA degradation (Ambros, V. (2001) microRNAs: tiny regulators with great potential. Cell 107(7):823-6; Buckingham, S. (2003) The major world of microRNAs, Horizon Symposia: Understanding the RNAissance. Nature Publishing Group, Nature, 1-3; He et al. (2009) Let-7a elevates p21$^{WAF1}$ levels by targeting of NIRF and suppresses the growth of A549 lung cancer cells. FEBS Letters 583:3501-3507). miRNAs regulate a wide range of biological processes, including developmental timing, apoptosis, differentiation, cell proliferation and metabolism and both upregulation and downregulation of miRNAs have been implicated in a variety of pathological conditions. miRNAs often form multi-gene families with common mRNAs targets.

microRNA names are assigned using the prefix "mir" or "miR" and followed by a dash and a number. The uncapitalized "mir" prefix generally refers to the pre-miRNA, while a capitalized "miR" prefix usually refers to the mature form. miRNAs with nearly identical sequences except for one or two nucleotides are typically annotated with an additional lower case letter.

miRNAs are transcribed in the nucleus as large RNA hairpin precursors called pri-miRNAs. The pri-miRNAs are processed in the nucleus by a microprocessor complex to generate double-stranded intermediates referred to as pre-miRNAs, which are approximately 70-nucleotides in length. The pre-miRNAs are then exported into the cytoplasm where they are assembled into cytoplasmic protein-RNA complexes referred to as RNA-induced silencing complexes (RISCs). The complex-bound single-stranded miRNA binds to target mRNA with sequences that are at least partially complementary to the miRNA. A key specificity determinant for miRNA target recognition is based on Watson-Crick pairing of the "seed" region in the mature miRNA (e.g., within nucleotides 2-7 or 2-8 of the mature miRNA) to the "seed match site" in the target 3'UTR of the mRNA, within the target 5'UTR, or within a portion of the coding region, which nucleates the miRNA:target mRNA interaction. In this manner, each miRNA may regulate hundreds to thousands of mRNA species. Additionally, many miRNAs are members of highly related families that contain identical seeds.

In one embodiment, miRNA are used in connection with recombinant polypeptide production in a mammalian cell culture. In one embodiment, a recombinant polypeptide is produced using mammalian cells that have modified activity for miRNA that are involved in apoptosis, protein translation, cellular metabolism, cellular proliferation and/or stress response. In one embodiment, the mammalian cells or cell culture have increased activity or expression of a particular miRNA involved in apoptosis, protein translation, cellular metabolism, cellular proliferation and/or stress response. In another embodiment, the mammalian cells or cell culture have decreased activity or expression of a particular miRNA involved in apoptosis, protein translation, cellular metabolism, cellular proliferation and/or stress response.

In one embodiment, mammalian cells are engineered for increased or decreased miRNA activity. As used herein "miRNA activity" refers to the ability of miRNA to regulate biological processes, such as developmental timing, apoptosis, differentiation, cell proliferation and metabolism by binding to target messenger RNA. miRNA activity of a particular miRNA can be increased, for example, by increasing the amount of that particular miRNA present in the cell or cell culture. For example, methods are known for increasing miRNA expression in a cell, including, but not limited to, miRNA precursor transfection, including transfection of pri-miRNA or pre-miRNA, transfection of miRNA oligonucleotides and vector based overexpression of miRNA, including the use of viral vectors and the generation of transgenic animals. For example, miRNA activity of a particular miRNA can be increased by transfecting a cell or cell culture with a single stranded miRNA oligonucleotide or with an expression vector encoding the miRNA oligonucleotide or precursor thereof. In one embodiment, the cell is transfected with a synthetic miRNA oligonucleotide. In some embodiments, the synthetic miRNA oligonucleotide includes one or more chemical modifications, for example, to improve nuclease resistance, to increase resistance to miRNA-directed cleavage by RISC and/or to increase binding affinity. In some embodiments, the miRNA oligonucleotide can be conjugated to a targeting agent to facilitate uptake of the oligonucleotide by cells. In one embodiment, the cells are modified to increase activity of one or more miRNA selected from miR-10a [SEQ ID NO: 1 (uacccuguagauccgaauuugug)], miR-21 [SEQ ID NO: 2-uagcuuaucagacugauguuga] and combinations thereof. In another embodiment, the cells are modified to over-express one or more miRNA selected from miR-10a, miR-21, and combinations thereof. In one embodiment, the cells are modified to overexpress one or more miRNA selected from miR-10a, miR-21, and combinations thereof at least about 10 fold, 25 fold, 50 fold, 100 fold, 200 fold, 300 fold, 400 fold, 500 fold, 600 fold, 700 fold, 800 fold, 900 fold, 1000 fold and up to about 1100 fold, 1200 fold, 1300 fold, 1400 fold, 1500 fold or more as compared to a cell line that has not been modified to over-express one or more of these miRNA. In a more particular embodiment, the cells are transfected, either stably or transiently, with a vector capable of expressing miR-10a and/or miR-21.

Alternately, miRNA activity of a particular miRNA can be inhibited or decreased, for example, by decreasing the amount of that particular miRNA present in the cell or cell culture. Methods for decreasing the amount of a particular miRNA present in a cell or cell culture include genetic knockouts or the use of miRNA inhibitors. In one embodiment, the activity of a particular miRNA is decreased by culturing one or more genetically engineered cells in which the endogenous gene encoding the particular miRNA has been knocked out (i.e., the gene encoding the miRNA has been replaced or disrupted). Methods for generating genetic knockouts are known. In another embodiment, the activity of a particular miRNA in a cell or cell culture is decreased by culturing the cell or cell culture in the presence of miRNA inhibitor. As used herein, the term "miRNA inhibitor" refers to a molecule that can suppress miRNA regulation of target gene expression, for example, a molecule that can suppress native or endogenous miRNA activity. In one embodiment, the mammalian cells are transfected, either stably or transiently, with an expression vector encoding miRNA inhibitor or precursor thereof. In another embodiment, a mammalian cell or cell culture can be transfected with a single stranded antisense miRNA inhibitor oligonucleotide. In one embodiment, the oligonucleotide is a synthetic oligonucleotide. In some embodiments, the synthetic oligonucleotide includes one or more chemical modifications, for example, to improve nuclease resistance, to increase resistance to miRNA-directed cleavage by RISC and/or to increase binding affinity. In one embodiment, the miRNA oligonucleotide can be conjugated to a targeting agent to facilitate uptake of the oligonucleotide by cells.

In one embodiment, the miRNA inhibitor includes an anti-miRNA antisense oligonucleotide (anti-miR) that is able to tightly bind to and thereby sequester the miRNA in competition with cellular target mRNAs, leading to functional inhibition of the miRNA. Because many miRNAs are members of highly related families that contain identical seeds, a single anti-miR can block the function of more than one miRNA in a family. In one embodiment, the anti-miR includes a single antisense unit. In another embodiment, the anti-miR includes multiple antisense units engineered into a single oligonucleotide that is able to simultaneously silence multiple miRNA targets. In yet another embodiment, more than one anti-miR can be co-transfected to target various isoforms or family members. In still another embodiment, more than one anti-miR can be co-transfected to target more than one microRNA. Chemical modifications to improve nuclease resistance, to increase resistance to miRNA-directed cleavage by RISC and/or to increase binding affinity of the antisense oligonucleotide to the miRNA are known, and include, for example, modifications of the sugar, the base or the internucleotide linkages. One example of a chemically modified anti-miR is a single-stranded inhibitor containing 2'-O-methyl ribose sugars. 2'-O-methyl oligonucleotides are resistant to cleavage by both RISC and other nucleases and form more thermodynamically stable RNA:RNA duplexes as compared to unmodified antisense oligonucleotides. In another embodiment, the inhibitor can include a single-stranded 2'-O-methyl-modified oligoribonucleotide having multiple antisense units engineered into a single fragment that is able to simultaneously silence multiple miRNA targets. Other chemical modifications include 2'-O-methoxyethyl and 2'-fluoro modifications at the 2' position of the sugar moiety. In another embodiment, the anti-miR can include modification of the furanose ring in the sugar phosphate backbone (sometimes referred to as a "locked nucleic acid"). Nuclease resistance can also be improved by backbone modification of the parent phosphodiester linkage into phosphorothiate (PS) linkages in which a sulfur atom replaces one of the non-bridging oxygen atoms in the phosphate group or by using morpholino oligomers in which a six-membered morpholine ring replaces the sugar moiety.

In another embodiment, the miRNA inhibitor can include miRNA "sponge" technology, which can be used for transient and/or stable inhibition of miRNA in cultured cells, including entire miRNA seed families. A miRNA sponge is an expression vector that can be used to transfect mammalian cells and express miRNA antisense sequences that include multiple (i.e., at least about 5, at least about 10 or between about 5 and about 20) miRNA binding sites that are complementary to one or more target miRNAs. When a vector encoding a miRNA sponge is transfected into cultured cells, the RNA expressed by the sponge compete with endogenous mRNA for binding to the particular microRNA, thus able to derepress microRNA mRNA targets. In one embodiment, a single sponge can be used to block an entire microRNA seed family.

In another embodiment, the miRNA inhibitor includes a miRNA masking antisense oligonucleotide (miR-mask). In one embodiment, the miRNA masking antisense oligonucleotide includes a single-stranded oligonucleotide (for example, a chemically modified 2'-O-methyl-modified oligoribonucleotide) that, rather than directly interacting with the target miRNA, is fully complementary to and binds to a binding site of the particular miRNA in the 3' UTR of the target mRNA. In this way, the miR-mask blocks access of the target miRNA to the binding site to derepress the target gene. In another embodiment, the inhibitor can include a combination of the aforementioned technologies. For example, sponge/miR-mask technology combines the principle of action of the miRNA sponge and the miR-mask technologies for targeting miRNAs.

In one embodiment, the cells have reduced activity of one or more miRNA selected from miR-let7a [SEQ ID NO: 3 (ugagguaguagguuguauagu)], miR-16 [SEQ ID NO: 4 (uagcagcacguaaauauuggcg)], miR-101 [SEQ ID NO: 5 (uacaguacugugauaacugaa)], miR-145 [SEQ ID NO: 6 (guccaguuuucccaggaaucccu)], miR-143 [SEQ ID NO: 7 (ugagaugaagcacuguagcuc)] and combinations thereof. In one embodiment, the cells under-express one or more miRNA selected from miR-let-7a, mir-16, miR-101, miR-145, miR-143, and combinations thereof. In one embodiment, the cells include genetic knockouts of one or more miRNA selected from miR-let-7a, mir-16, miR-101, miR-145, miR-143 and combinations thereof. In another embodiment, the cells are transfected, either stably or transiently, with a vector capable of expressing one or more anti-miR inhibitors selected from anti-miR-let7a [SEQ ID NO: 8 (ACTATACAACCTAC-TACCTCA)], anti-miR-16 [SEQ ID NO: 9 (CGCCAAT-ATTTACGTGCTGCTA)], anti-miR-101 [SEQ ID NO: 10 (TTCAGTTATCACAGTACTGTA)], anti-miR-145 [SEQ ID NO: 11 (AGGGATTCCTGGGAAAACTGGAC)guccaguuuucccaggaaucccu], miR-143 [SEQ ID NO: 12 (GAGC-TACAGTGCTTCATCTCA)] and combinations thereof. Activity of miRNA can be quantified by looking at targets of the miRNA at the protein and RNA level. For example, reporter assays for miRNA activity, such as GFP or Luciferase with a miRNA site in the construct 3'UTR can be utilized. In one embodiment, one or more anti-miR inhibitors selected from anti-miR-let7a, anti-miR-16, anti-miR-101, anti-miR-145, miR-143 or a combination thereof is overexpressed at least about 10 fold, 25 fold, 50 fold, 100 fold, 200 fold, 300 fold, 400 fold, 500 fold, 600 fold, 700 fold, 800 fold, 900 fold, 1000 fold and up to about 1100 fold, 1200 fold, 1300 fold, 1400 fold, 1500 fold or more as compared to a cell line that has not been modified to express the inhibitor.

In another embodiment, activity of at least one mediator of apoptosis, protein and/or cellular metabolism is increased or decreased in a cell culture having reduced miRNA-let-7a activity. In one embodiment, activity of one or more miRNA selected from miR-10a, miR-21 and combinations thereof is increased in a cell culture having reduced miRNA-let-7a activity and/or activity of one or more miRNA selected mir-16, miR-101, miR-145, miR-143 and combinations thereof is decreased in a cell culture having reduced miRNA-let-7a activity. In one embodiment, expression of at least one target of miRNA-let-7a is increased in the cell culture having reduced miRNA-let-7a activity. In one embodiment, at least one target of miRNA-let-7a is selected from HMGA2, MYC, NF2, NIRF, RAB40C, and eIF4a.

Methods for measuring expression of mRNA are known and include, for example, PCR, RNase protection, southern blot, and in situ hybridization.

In another embodiment, expression of more than one miR can be altered (either increased or decreased, independently), for example, expression of at least 2, at least 3, at least 4 or up to 5 miRNA can be altered within a mammalian cell line to increase productivity by addressing multiple areas at once. In one embodiment, miR-let-7a activity may be decreased and the activity of a second miR can be altered. In one embodiment, the second miR can include miR-21, miR-10a and/or anti-miR-143.

D. Vectors

In one embodiment, a recombinant polypeptide is produced using mammalian cells that have been transfected, either stably or transiently, with a vector capable of expressing one or more miRNA or inhibitors of miRNA that are involved in apoptosis, protein translation, cellular metabolism, cellular proliferation and/or stress response. As used herein, the term "vector" refers to composition of matter which can be used to deliver a nucleic acid of interest to the interior of a cell. Numerous vectors are known including, but not limited to, linear polynucleotides, polynucleotides associated with ionic or amphiphilic compounds, plasmids, and viruses. The term "vector" can include an autonomously replicating plasmid or a virus or a vector or plasmid that is not autonomously replicating. In one embodiment, the vector can be a naked RNA polynucleotide, a naked DNA polynucleotide, a poly-lysine-conjugated DNA or RNA, a peptide-conjugated DNA or RNA, a liposome-conjugated DNA, which are not autonomously replicating. In one embodiment, the vector is a synthetic oligonucleotide. It is contemplated that any vector may be used for transient transfection as long as it is expressed in the appropriate system and viable in the host. For stable transfection, the vector is generally replicable in the host. Large numbers of suitable vectors are known and are commercially available.

In one embodiment, the vector includes at least one polynucleotide encoding a miRNA or miRNA inhibitor, or a precursor thereof, operably linked to a promoter. The phrase "operably linked" means that the promoter is in the correct location and orientation in relation to a polynucleotide to control initiation of transcription by RNA polymerase and expression of the polynucleotide. As used herein, the term "regulatory sequence" refers to a nucleic acid sequence that controls some aspect of the expression of a nucleic acid sequence that is operably linked to the regulatory sequence. In some instances, the regulatory sequence may be a promoter (i.e., a regulatory element that facilitates initiation of transcription of an operably linked coding region) and in other instances, the regulatory sequence may include an enhancer sequence and/or other regulatory element, such as ribosome binding sites, splicing signals, polyadenylation signals, transcription termination sequences and/or 5' flanking non-transcribed sequences. The promoters employed in the vector may be constitutive or inducible. A "constitutive" promoter is a nucleotide sequence which, when operably linked to a polynucleotide that encodes a gene product, causes the gene product to be produced in a cell under most or all physiological conditions of the cell (i.e., a specific stimulus is not required). An "inducible" promoter is a promoter that is capable of directing a level of transcription of an operably linked polynucleotide sequence in the presence of a stimulus (e.g., heat shock, chemicals, light, etc.) that is different from the level of transcription of the operably linked polynucleotide sequence in the absence of the stimulus. The regulatory element may be "endogenous" or "exogenous" or "heterologous." An "endogenous" regulatory element is one that is naturally linked to a particular nucleic acid sequence. An "exogenous" or "heterologous" regulatory element is one that is placed in juxtaposition to a nucleic acid sequence by means of genetic manipulation such that transcription of the nucleic acid sequence is directed by the linked regulatory element.

Examples of suitable promoters include promoters known to control expression of genes in mammalian cells, including, but not limited to, viral promoters such as the cytomegalovirus (CMV) immediate early promoter, herpes simplex virus thymidine kinase (HSV-TK) promoter, simian virus 40 (SV40) promoter or rous sarcoma varus (RSV) LTR promoter, pMC1, phosphoglycerate kinase (PGK) promoter, U1 promoter, and H6 promoter In addition to encoding one or more miRNA or miRNA inhibitors, the vector may also include selectable marker genes, reporter genes, or genes encoding a recombinant polypeptide of interest. Additionally, expression vectors used for stable transfection may include one or more sites for stable integration into a host cell genome.

In one embodiment, the expression vector includes one or more selectable markers or reporter genes to assess delivery and duration of action of the vector in vitro. The term "selectable marker" refers to a gene that encodes an enzyme having an activity that confers resistance to an antibiotic or other drug upon the cell in which the selectable marker is expressed. Examples of selectable markers include, but are not limited to, adenosine deaminase (ADA), aminoglycoside phosphotransferase, bleomycin, cytosine deaminase, dihydrofolate reductase, histidinol dehydrogenase, hygromycin-B-phosphotransferase, puromycin-N-acetyl transferase, thymidine kinase, xanthine-guanine phosphoribosyltransferase, ampicillin, neomycin, kanamycin, zeocin, and carbenicillin.

The term "reporter gene" refers to a gene encoding a protein whose expression can readily be detected (e.g., luminescence or fluorescence). Examples of reporter genes include, but are not limited to, green fluorescent protein, luciferase, chloramphenicol acetyltransferase, β-galactosidase, alkaline phosphatase, horse radish peroxidase, RFP, YFP, and BFP. In one embodiment, the expression vector is a viral vector, including, but not limited to, adenoviral vectors, adeno-associated virus vectors, retroviral vectors, such as lentiviral vectors or Moloney murine leukemia virus, and vectors derived from poxvirus, herpes simplex virus I. In another embodiment, the expression vector is a non-viral vector. Examples of suitable vectors include, but are not limited to, the following eukaryotic vectors: pWLNEO, pSV2CAT, pOG44, PXT1, pSG (Stratagene) pSVK3, pBPV, pMSG, pSVL (Pharmacia), and pCS2 vectors and its derivatives.

In one embodiment, a recombinant polypeptide is produced using mammalian cells that have been transfected, either stably or transiently, with one or more vectors capable of expressing one or more miRNA selected from miR-10a, miR-21 and precursors thereof or combinations thereof. In a more particular embodiment, a recombinant polypeptide is produced using mammalian cells that have been transfected, either stably or transiently, with one or more vectors capable of expressing one or more antisense oligonucleotides selected from anti-miR-let7a, anti-miR-16, anti-miR-101, anti-miR-145, anti-miR-143 and precursors thereof, or combinations thereof. In one embodiment, the mammalian cells have been transfected, either stably or transiently with one or more vectors capable of expressing at least one miRNA and at least one miRNA inhibitor. In yet another embodiment, the mammalian cells have been transfected with one or more vectors capable of expressing at least one miRNA and/or at least one miRNA inhibitor in combination with at least one polynucleotide encoding a recombinant polypeptide of interest.

E. Transfection

The vectors described herein can be introduced into a mammalian host cell using methods known in the art. The term "transfection" refers to the introduction of exogenous genetic material into cells to produce genetically modified cells. For example, a vector can be transferred into a host cell by physical, chemical or biological means. Physical methods for introducing a polynucleotide into a host cell include, but are not limited to, calcium phosphate precipitation, lipofection (including positively charged liposome mediated transfection), particle bombardment, microinjection, DEAE-dextran mediated transfection and electroporation. Biological methods for introducing a vector into a host cell include the use of DNA and RNA vectors, including, for example, viral vectors. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes.

In one embodiment, the host cell can be stably transfected with the vector. The term "stable transfection" means that the nucleotide sequence in the vector is able to integrate into the full DNA sequence of a mammalian cell. Typically, for stable transfection, a host cell is transfected with a vector that includes a selectable marker. In one embodiment, the selectable marker is co-expressed on the same vector as the miRNA or miRNA inhibitor or precursor thereof. In another embodiment, the selectable marker is expressed on a separate co-transfected vector. Growth of the transfected cells in the presence of the selecting agent allows the subpopulation of cells in which the exogenous genetic material has been incorporated into the genome to persist. Typically selection pressure is maintained for at least about 1 week, at least about 2 weeks and up to about 3 weeks or up to about 1 month. At the end of the selection period, the cells that are viable in the selective medium will have integrated the exogenous genetic material from the expression plasmid. Integration of the exogenous genetic material can be confirmed by the presence of a reporter and the cells can be expanded for large scale culturing.

In another embodiment, the host cell can be transiently transfected with the vector. In contrast to stable transfection, transiently transfected genetic material is only expressed in the transfected cells for a limited period of time and does not integrate into the genome of the host cell. In general, transient transfection results in expression of the miRNA, anti-miR inhibitor or precursor thereof for at least about 24 hours, at least about 48 hours, at least about 72 hours and up to about 96 hours.

F. Cell Culture

The term "cell culture" refers to the growth and propagation of cells outside of a multicellular organism or tissue. Cell culture conditions such as pH, temperature, humidity, atmosphere and agitation can be varied to improve growth and/or productivity characteristics of the cell culture. In general, mammalian cell cultures are maintained at a pH between about 6.5 and about 7.5 at a temperature of between about 36° C. and about 38° C., typically at about 37° C. and a relative humidity of between about 80% and about 95%. Mammalian cell culture media typically contain buffering systems that require a carbon dioxide ($CO_2$) atmosphere of between about 1% and about 10%, typically between about 5% and about 6%. Mammalian cells may be cultured in suspension or while attached to a solid substrate. Mammalian cells can be cultured in small scale cultures, for example, in a laboratory in 100 ml containers or in 250 ml containers, generally having a volume within the container not exceeding 40% of the total vessel volume, and usually about 25%. Alternatively, the cultures can be large scale, for example, 1000 ml containers 3000 ml, 8000 ml containers, and 15000 ml containers, or in a large scale bioreactor, for example, in a manufacturing facility, at volumes of up to 1000 L, up to 5000 L and up to 10,000 L. Large scale production of recombinant polypeptides by mammalian cells can include continuous, batch and fed-batch culture systems. Mammalian cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode. Large scale cell cultures are typically maintained for days, or even weeks, while the cells produce the desired protein product(s).

The methods described herein may be used to improve production of recombinant polypeptides in both single phase and multiple phase culture processes. In one embodiment, the cell culture is a multiple stage process in which the cells are first cultured in a growth phase, under environmental conditions that maximize cell proliferation and viability and then transferred to a production phase, under conditions that maximize polypeptide production. The growth and production phases may be preceded by, or separated by, one or more transition phases. In one embodiment, the cell culture is a multiple stage process having at least one growth phase and at least one production phase. In one embodiment, the cells are incubated at a higher temperature during the growth phase as compared to the production phase. For example, the cells may be cultured during a growth phase at a first temperature between about 35° C. to about 38° C., and cultured during a production phase at a second temperature between about 29° C. to about 37° C., or between about 30° C. to about 36° C., or between about 30° C. to about 34° C. In addition, chemical inducers of protein production, such as, for example, caffeine, butyrate, and hexamethylene bisacetamide (HMBA), may be added during the production phase. In one embodiment, activity of a miRNA or a miRNA inhibitor is increased or decreased during the production phase. In one embodiment, transcription of an expression vector encoding miRNA or a miRNA inhibitor or precursor thereof is induced during the production phase. In another embodiment, miRNA or a miRNA vector or oligonucleotide, or inhibitor or precursor thereof, is added to the culture media during the production phase.

The mammalian cell lines (also referred to as "host cells") can be genetically engineered to express a recombinant polypeptide, for example, a polypeptide of commercial or scientific interest. Genetically engineering a cell line generally involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired recombinant polypeptide. Methods and vectors for genetically engineering cells and/or cell lines to express a polypeptide are known. Examples of mammalian cells suitable for production of recombinant polypeptides include, but are not limited to, Chinese hamster ovary (CHO) cells, mouse myeloma (NS0), human embryonic kidney (HEK 293), baby hamster kidney (BHK) cells, Vero cells, HeLa cells, Madin-Darby Canine Kidney (MDCK) cells, CV1 monkey kidney cells, 3T3 cells, myeloma cell lines such as NS0 and NS1, PC12, WI38 cells, COS cells (including COS-1 and COS-7), and C127. In one embodiment, the mammalian cell line expresses an increased or decreased level of one or more miRNAs. In one embodiment, the mammalian cells are transfected, either stably or transiently, with heterologous miRNA or an anti-miRNA inhibitor as described in more detail above. In a more particular embodiment, the mammalian cells in the cell culture have decreased miRNA-let-7a activity. In one embodiment, the mammalian cells are transfected with an anti-miRNA-let-7a inhibitor.

The mammalian cells can be maintained in a variety of cell culture media. The term "cell culture medium" refers to a nutrient solution in which cells, for example, mammalian cells, are grown. Cell culture media formulations are well known in the art. Typically, cell culture media include buffers, salts, carbohydrates, amino acids, vitamins and trace essential elements. The cell culture medium may or may not contain serum, peptone, and/or proteins. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters. Various culture media, including serum-free and defined culture media, are commercially available, and include, but are not limited to, Minimal Essential Medium (MEM, Sigma, St. Louis, Mo.); Ham's F10 Medium (Sigma); Dulbecco's Modified Eagles Medium (DMEM, Sigma); Minimal Essential Medium (MEM); Basal Medium Eagle (BME); RPMI-1640 Medium (Sigma); HyClone cell culture medium (HyClone, Logan, Utah); and chemically-defined (CD) media, which are formulated for particular cell types, e.g., CD-CHO Medium (Invitrogen, Carlsbad, Calif.). Supplementary components or ingredients, such as those described above, can be added to commercially available media. In one embodiment, the culture media can include miRNA or miRNA inhibitor oligonucleotides or precursors thereof or expression vectors encoding miRNA or miRNA inhibitors or precursors thereof.

The recombinant polypeptides expressed by the mammalian cell culture may be produced intracellularly or be secreted into the culture medium from which they can be recovered and/or collected. In addition, the recombinant polypeptides can be purified, or partially purified, from the culture using known processes and products available from commercial vendors. The purified polypeptides can then be "formulated", for example, buffer exchanged, sterilized, bulk-packaged, and/or packaged for a final user.

Production characteristics of a cell culture can be determined by measuring viable cell density (VCD), antibody titer, and productivity, including specific productivity (Qp), cumulative productivity and maximum productivity evaluated at peak VCD.

In one embodiment, the cell culture includes mammalian cells having reduced miRNA-let-7a activity. In one embodiment, the miRNA-let-7a activity is reduced by a microRNA inhibitor. In one embodiment, the microRNA inhibitor is an antisense oligonucleotide inhibitor of miRNA-let-7a. In one embodiment, the mammalian cells are transfected with a replicable expression vector encoding the antisense inhibitor of miRNA-let-7a. In another embodiment, the mammalian cells are transfected with an oligonucleotide inhibitor of miRNA-let-7a. In one embodiment, the oligonucleotide inhibitor is chemically modified, for example, to improve nuclease resistance, to increase resistance to miRNA-directed cleavage by RISC and/or to increase binding affinity. In one embodiment, the mammalian cells having reduced miRNA-let-7a include miRNA-let-7a genetic knockouts.

In one embodiment, the cell culture has a productivity that is increased at least about 25% compared to a control cell culture that does not have reduced miRNA-let-7a activity. As used herein, the term "productivity" refers to the concentration of recombinant polypeptide produced by a cell culture over a defined period of time. Productivity can be evaluated based on measurements such as titer, viable cell density (VCD), and % viability. Methods for measuring titer, VCD, and % viability are known. In one embodiment, the cell culture has a specific productivity that is increased at least about 25%, 30%, 35%, 40%, 45%, 50%, 55%, 60%, 65%, 70%, 75% and up to about 100%; between about 25% and about 100%; between about 50% and about 75% when compared to a control cell culture that does not have reduced miRNA-let-7a activity.

In one embodiment, productivity refers to a specific productivity (Yoon et al., (2006) Biphasic culture strategy for enhancing volumetric erythropoietin productivity of Chinese hamster ovary cells. Enzyme and Microbial Technology 39:362-365; Baumann et al., (2008) Hypoxic fed-batch cultivation of *Pichia pastoris* increases specific and volumetric productivity of recombinant proteins. Biotechnology and Bioengineering 100(1):177-183; Brezinsky et al., (2003) A simple method for enriching populations of transfected CHO cells for cells of higher specific productivity. Journal of Immunological Methods 277:141-155; Fox et al., (2003) Maximizing Interferon-γ production by Chinese hamster ovary cells through temperature shift optimization: experimental and modeling. Biotechnology and Bioengineering 85(2):177-184; Wurm, (2004) Production of recombinant protein therapeutics in cultivated mammalian cells. Nature Biotechnology 22(11):1393-1398; Browne and Al-Rubeai, (2009 Selection methods for high-producing mammalian cell lines. In: Al-Rubeai M, editor. *Cell Line Development*, Series: Cell Engineering 6, Springer Science+Business Media B.V. p. 127-151). As used herein, the term "specific productivity" refers to recombinant protein produced per viable cell in culture per day and can be calculated as the slope of the product concentration (titer) versus the integral of cumulative viable cell density (mg/L/CCD). In one embodiment, the cell culture has a specific productivity that is increased at least about 25%, 30%, 35%, 40%, 45%, 50%, 55%, 60%, 65%, 70%, 75% and up to about 100%; between about 25% and about 100%; between about 50% and about 75% when compared to a control cell culture that does not have reduced miRNA-let-7a activity.

In one embodiment, productivity refers to "maximum productivity" determined at peak viable cell density (VCD). As used herein, the term "maximum productivity" refers to the level of productivity when the culture is at its maximum VCD and can be calculated as the change in titer at maximum VCD compared to the previous timepoint divided by the change in VCD between the maximum and previous timepoints multiplied by the number of days in culture from timepoint 1 to timepoint 2 divided by the natural log of the final VCD over the initial VCD. In one embodiment, the maximum productivity is increased at least about 25% when compared to a control cell culture that does not have reduced miRNA-let-7a activity. In one embodiment, the cell culture has a maximum productivity that is at least about 25%, 30%, 35%, 40%, 45%, 50%, 55%, 60%, 65%, 70%, 75%, 80%, 85%, 90%, 95%, 100%, 125%, 150%, 175% or 200% or between about 25% and about 200% when compared to a control cell culture that does not have reduced miRNA-let-7a activity.

In one embodiment, productivity refers to cumulative productivity. As used herein, the term "cumulative productivity" refers to specific productivity throughout the full growth cycle and can be calculated as the slope of product concentration (titer) versus the integral of cumulative viable cell density (mg/L/CCD) (Renard et al., (1988) Evidence that monoclonal antibody production kinetics is related to the integral of the viable cells curve in batch systems. Biotechnology Letters 10(2):91-96; Yoon et al., (2006) Biphasic culture strategy for enhancing volumetric erythropoietin productivity of Chinese hamster ovary cells. Enzyme and Microbial Technology 39:362-365; Li et al., (2010) Cell culture processes for monoclonal antibody production. mAbs 2(5)466-477; Breszinsky et al., (2003) A simple method for enriching populations of transfected CHO cells for cells of higher specific productivity. Journal of Immunological Methods 277:141-155; Fox et al., (2003) Maximizing Interferon-γ production by Chinese hamster ovary cells through temperature shift optimization: experimental and modeling. Biotechnology and Bioengineering 85(2): 177-184). In one embodiment, the cell culture has a cumulative productivity that is increased at least about 25%, 30%, 35%, 40%, 45%, 50%, 55%, 60%, 65%, 70%, 75% and up to about 100%; between about 25% and about 100%; between about 50% and about 75% when compared to a control cell culture that does not have reduced miRNA-let-7a activity.

In one embodiment, productivity refers to the specific productivity of the culture, i.e., the titer of the recombinant polypeptideper cell in a total culture as compared to the titer of the recombinant polypeptide in a control cell culture.

G. Recombinant Polypeptides

The term "recombinant polypeptide" as used herein refers to a genetically engineered polypeptide or protein produced by a cultured host cell. As used herein, the term "heterologous" refers to a recombinant polypeptide that is produced by a host cell that does not normally express that polypeptide. However, a heterologous polypeptide can include polypeptides that are native to an organism, but that have been intentionally altered in some manner. For example, a heterologous polypeptide can include a polypeptide that is expressed by a host cell that has been transfected with a vector that expresses the polypeptide.

In one embodiment, the polypeptide is an antibody or binding fragment thereof. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')$_2$ single stranded antibody (svFC), dimeric variable region (Diabody) and disulphide-linked variable region (dsFv). Immunoglobulin molecules can be of any type (e.g., IgG, IgE, IgM, IgD, IgA and IgY), class (e.g., IgG1, IgG2, IgG3, IgG4, IgA1 and IgA2) or subclass.

In another embodiment, the recombinant polypeptide is a non-antibody protein. Examples of non antibody proteins include, but are not limited to, fusion proteins, receptors, ligands of cell surface proteins, secreted proteins, and enzymes.

H. Kits

Any of the miRNA or anti-miRNA oligonucleotides or expression vectors and additional components, such as, buffer, cells, and culture medium can be packaged in the form of a kit. Typically, a kit also contains materials such as instructions for performing the methods of the invention, packaging material, and a container. In one embodiment, the kit includes at least one expression vector encoding a miRNA gene product or an miRNA inhibitor, as described in more detail above. In one embodiment, the expression vector can be used in in vitro transcription or transcription/translation systems, or used to transfect cells, either transiently or stably. In another embodiment, the kit includes at least two expression vectors, one of which encodes a miRNA gene product or a miRNA inhibitor and the other encodes a selectable marker, a reporter gene or a recombinant polypeptide.

I. Incorporation by Reference

All references cited herein, including patents, patent applications, papers, text books, and the like, and the references cited therein, to the extent that they are not already, are hereby incorporated herein by reference in their entirety.

J. Equivalents

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

6. WORKING EXAMPLE

To investigate the ability of altered microRNA expression to improve mammalian cell productivity, two antibody-producing CHO cell lines were stably transduced with lentiviral vectors encoding nine different microRNAs or anti-sense microRNAs inhibitors based on potential involvement of the microRNA in pathways involved in recombinant polypeptide production, such as cellular proliferation, stress response, apoptosis, and mRNA translation (Table 1).

A. MATERIALS AND METHODS

Cell Culture and Transduction

Chinese hamster ovary (CHO) cells (suspension cell line) expressing various monoclonal antibodies were grown in CD CHO medium (Life Technologies, Carlsbad, Calif.) supplemented with 50 uM L-Methionine sulfoximine (MSX; Sigma Aldrich, St. Louis, Mo.) and 0.5×GS Supplement (SAFC Biosciences, Lenexa, Kans.). Shake flask cultures were maintained at 120RPM, 37° C., 6% $CO_2$ and 80% humidity. Two hundred fifty thousand cells were transduced with lentiviral vectors over-expressing miR-10a, miR-21 or a vector control (Open Biosystems, Huntsville, Ala.), or those expressing anti-miR-let7a, -16, -101 or -145 or a vector control (System Biosciences, Mountain View, Calif.) at an MOI of 2-20. Transduced cells were expanded and selected for 2-3 weeks in 5 ug/mL Puromycin. Utilizing green fluorescent protein (GFP) or red fluorescent protein (RFP) vector components (from anti-miR or miR vectors, respectively) cells were collected by fluorescence-activated cell sorting (FACS) and expanded for fed-batch cell culture. Transduction efficiency approached 100% (FIG. 11A). Marker gene expression was monitored and confirmed throughout the use of these modified cell lines, and quantitative RT-PCR demonstrated a high level of expression of both miRs and anti-miRs in the resulting stably transduced cell lines (Table 2).

Fed-batch assays were performed in triplicate in 125 mL shake flasks. Cells were seeded in 25 mL CD CHO media with supplements described above. Following the generation of stable miR-modified CHO cell lines, the cells were monitored every two days for 14 days for viable cell density (VCD) (Table 3), mAb titer (Table 4) and Qp resulting from altered miRNA expression (FIGS. 1-4). Viable cell density (VCD), % viability (% V) and cell size were monitored using a ViCELL Cell Viability Analyzer (Beckman Coulter, Indianapolis, Ind.). Antibody titer was measured using the Octet system (forteBIO/Pall Life Sciences, Menlo Park, Calif.). Cumulative Qp was calculated as the slope of product concentration (titer) versus the integral of cumulative viable cell density (mg/L/CCD) (Renard et al., (1988) Evidence that monoclonal antibody production kinetics is related to the integral of the viable cells curve in batch systems. Biotechnology Letters 10(2):91-96; Yoon et al., (2006) Biphasic culture strategy for enhancing volumetric erythropoietin productivity of Chinese hamster ovary cells. Enzyme and Microbial Technology 39:362-365; Li et al., (2010) Cell culture processes for monoclonal antibody production. mAbs 2(5)466-477; Breszinsky et al., (2003) A simple method for enriching populations of transfected CHO cells for cells of higher specific productivity. Journal of Immunological Methods 277:141-155; Fox et al., (2003) Maximizing Interferon-γ production by Chinese hamster ovary cells through temperature shift optimization: experimental and modeling. Biotechnology and Bioengineering 85(2):177-184). Maximum $Q_P$ was calculated as the change in titer at maximum VCD compared to the previous timepoint divided by the change in VCD between the maximum and previous timepoints multiplied by the number of days in culture from timepoint 1 to timepoint 2 divided by the natural log of the final VCD over the initial VCD. Titer, cumulative Qp and maximum Qp are all presented as relative units compared to baseline.

RNA Extraction and Real-Time PCR Analysis

Total RNA was extracted from $0.5-5\times10^6$ cells using a miRVana miRNA Isolation Kit (Life Technologies) according to the manufacturer's instructions. Concentration was determined by Nanodrop analysis and RNA quality assessed on an Agilent 2100 Bioanalyzer using the RNA 6000 Nano LabChip. For TaqMan analysis of over-expressed miRNAs, 100-300 ng total RNA was reverse transcribed to cDNA using Multiscribe RT and Megaplex RT primer pools (Life Technologies) according to manufacturer's instructions. The resulting cDNA was preamplified using TaqMan PreAmp Master Mix and Megaplex preamp primer pools (Life Technologies) in a reaction containing 12.5 µL 2× TaqMan PreAmp Master Mix, 2.5 µL 10× Megaplex PreAmp primers, 7.5 µL $H_2O$ and 2.5 µL RT product. After cycling, amplified samples were diluted 1:4 in DNA Suspension Buffer (TEKnova, Hollister, Calif.) and held at −20° C. or used immediately for PCR. Real-time PCR on the preamplified material was performed using TaqMan assays specific for miR-10a and miR-21 (ABI/Life Technologies, Carlsbad, Calif.). The expression of each miRNA was evaluated relative to U6 snRNA.

To prepare samples for loading into 48×48 dynamic array chips (Fluidigm, South San Francisco, Calif.), the reaction mix contained 2.5 µL 2× Universal Master Mix (ABI/Life Technologies), 0.25 µL Sample Loading Buffer (Fluidigm), and 2.25 µL pre-amplified cDNA. To prepare the primer/probes, the reaction mix contained 2.5 µL 20× TaqMan Gene Expression Assay and 2.5 µL Assay Loading Buffer (Fluidigm). Prior to loading the samples and assay reagents into the inlets, the chip was primed in the IFC Controller. Five microliters of sample prepared as described was loaded into each sample inlet of the dynamic array chip, and 5 µL of 10× gene expression assay mix was loaded into each detector inlet. Upon completion of the IFC priming and load/mixing steps, the chip was loaded on the BioMark™ Real-Time PCR System for thermal cycling.

Anti-miR expression was assessed using the QuantiMiR™ RT kit (System Biosciences) according to manufacturer's instructions. Reactions were diluted 1:10 in DNA Suspension Buffer (TEKnova) for SYBR Green Real Time PCR using miR-specific forward primers and a universal reverse primer (System Biosciences). Quantitative PCR reactions contained 1 µL diluted QuantiMir cDNA, 0.5 µL 10 uM Universal Reverse Primer, 1 µL 10 µM miRNA-specific Forward Primer, 15 µL 2× SYBR Green qPCR Mastermix buffer and 12.5 µL RNase-free $H_2O$. Thermal cycling was performed on an Applied Biosystems 7900 real-time PCR instrument. A melt analysis was included at the end of the run to verify amplification reaction specificity. U6 snRNA was used as an internal control.

For expression analysis of miR-let7a mRNA targets, cDNA was synthesized from 500 ng extracted total RNA using SuperScript® III First-Strand Synthesis SuperMix (Life Technologies) and random hexamers following the manufacturer's instructions. Preamplification was performed using TaqMan Gene Expression Assays and TaqMan PreAmp Master Mix. Reactions contained 5 µL of cDNA, 10 µL PreAmp Master Mix and 5 µL of 0.2× gene expression assay mix (comprised of all primer/probes to be assayed) for a final volume of 20 µL. Preamplified cDNA was assayed by Real-Time PCR with TaqMan Gene Expression Assays specific for target genes of interest and TaqMan Universal Master Mix (Life Technologies) using a BioMark™ instrument (Fluidigm), as indicated above for over-expressed miRs. β-actin and GAPDH were used as internal controls and data were evaluated using the delta-delta Ct method.

Western Blotting

Target protein alterations were assessed by Western analysis of lysed cultures with or without miRNA modifications. Cell lysates of antibody producing CHO cultures were prepared in RIPA Lysis and Extraction Buffer (Pierce) with HALT protease and phosphatase inhibitors (Pierce). Fifteen micrograms cell lysates were resolved on 4-12% NuPage gels (Life Technologies) in 1× MOPS running buffer (Life Technologies) under reducing conditions and transferred to PVDF membranes (Life Technologies). Membranes were blocked for 1 hr in Protein-Free T20 (PBS) Blocking Buffer (Thermo Scientific Pierce, Rockford, Ill.) and incubated overnight at 4° C. with a 1:500 dilution of rabbit anti-RAS (Cell Signaling, Danvers, Mass.) or a 1:333 dilution of mouse anti-GAPDH (abcam, Cambridge, UK) primary antibodies. Blots were incubated in fluorescent-labeled secondary antibodies: anti-rabbit 800CW (LI-COR, Lincoln, Nebr.) and anti-mouse 680LT (LI-COR) for RAS and GAPDH, respectively, in PBST 0.1%+0.02% SDS for 30 min at RT. Fluorescent signals and band intensities were captured and quantified using the Odyssey Imaging System (LI-COR) and Odyssey software (LI-COR).

Antibody Fidelity/Integrity Analysis

Antibodies from miR or anti-miR-modified lines were produced and purified using Protein A affinity chromatography. Reverse phase separation was carried out using an Agilent 1200 series instrument equipped with an Agilent Zorbax Poroshell SB300 C3 75×1.0 mm column. 2 µg protein sample was reduced and injected on the column. The column was equilibrated with 90% Solvant A (0.1% Formic Acid in $H_2O$) and 10% Solvent B (0.1% Formic Acid in Acetonitrile), and elution was achieved by step gradient from 10-60% B. The flow rate and temperature were maintained at 0.4 ml/min and 35° C. throughout the run.

Mass spectrometric analyses were carried out in a positive ion mode with a scan range of 300-3000 m/z on an Agilent 6520 LC/MS QTOF mass spectrometer (Agilent Technologies, Santa Clara, Calif.). The coupling between the LC and the TOF was via an electrospray ionization (ESI) source with dual nebulizers—one nebulizer for the LC eluent and one nebulizer for the internal reference mass compounds (m/z 322.0481 and m/z 1221.9906). The ESI mass spectra were analyzed using Agilent MassHunter Qualitative Analysis with Bioconfirm for automated deconvolution and protein confirmation.

B. RESULTS

Anti-miR-Let-7a Increases CHO Cell Productivity

Figure 1:
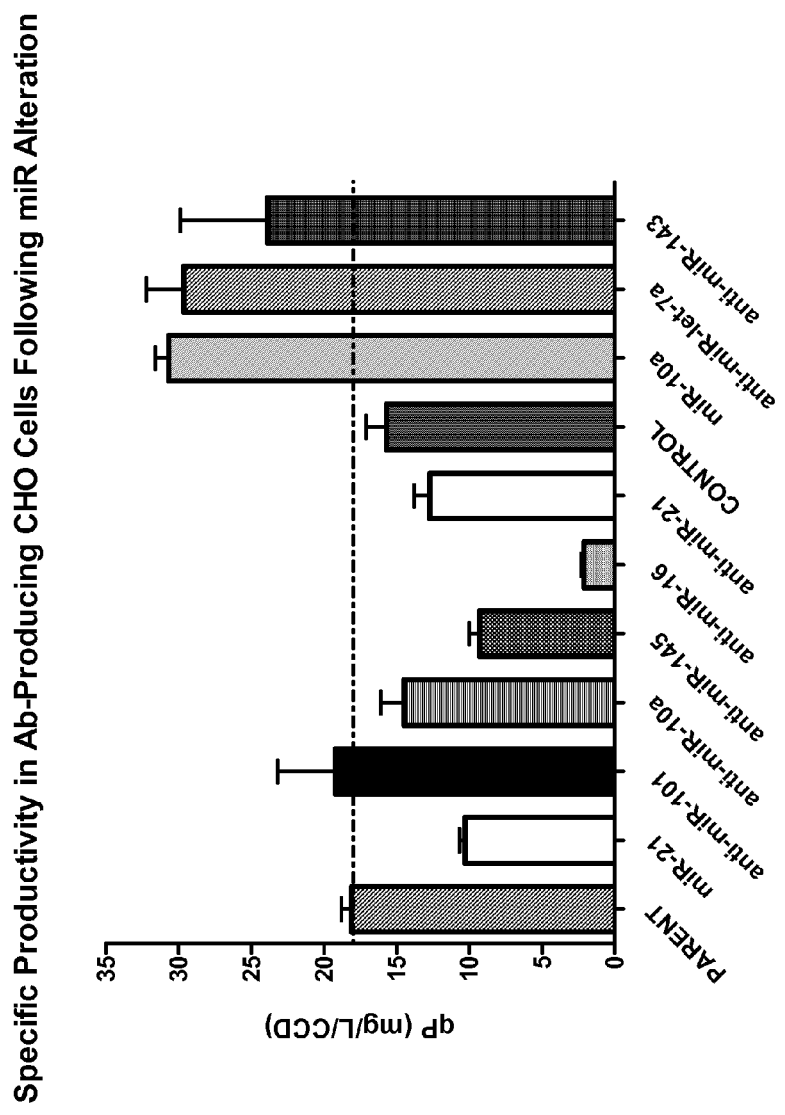
FIG. 1 is a graph showing end of run specific productivity ($Q_P$) calculated as titer/integral of cumulative VCD and reported as mg/L/cumulative cell day (CCD).
Figure 2:
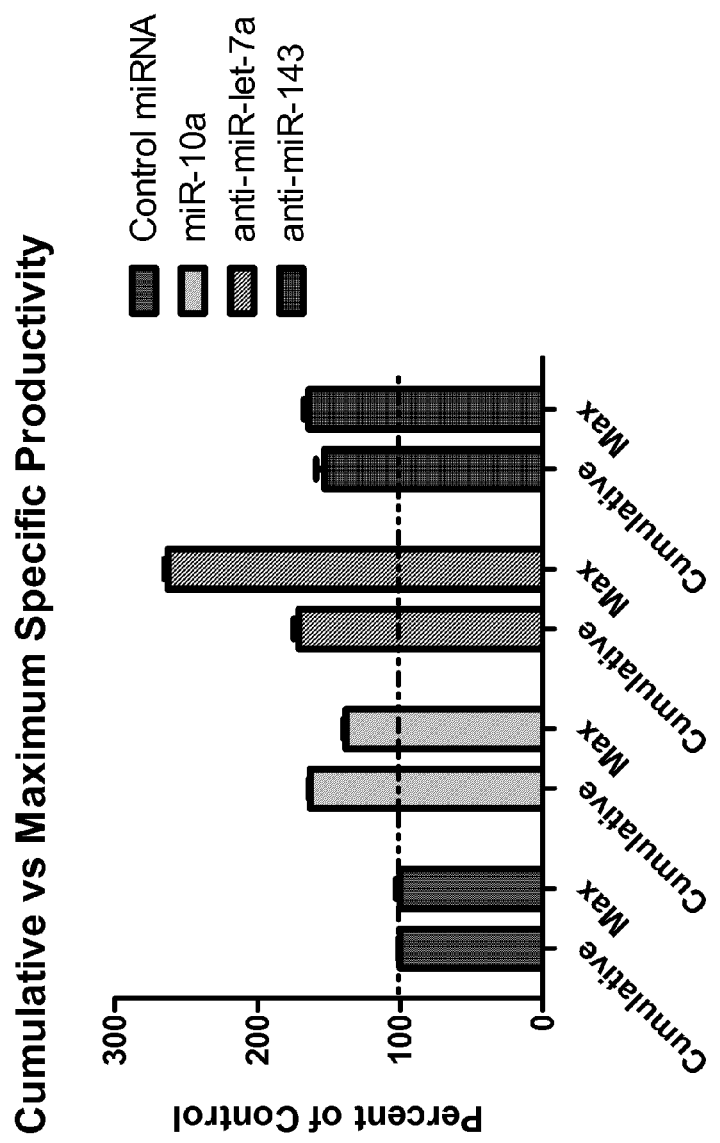
FIG. 2 is a graph showing Cumulative $Q_P$ compared to Maximum $Q_P$.

MiR-10a, anti-miR-let-7a and anti-miR-143 demonstrated the highest levels of cumulative Qp, with productivity increases of 63%, 71% and 53% compared to control lines, respectively (FIG. 1). In addition to evaluating cumulative Qp, we also evaluated the maximum Qp, calculated at peak VCD for each of these miR-modified cell lines. Results showed increases in maximum productivity of 38%, 163% and 64% for miR-10a, anti-miR-let-7a and anti-miR-143 compared to parent/control lines (FIG. 2), respectively. The additional miR-modified CHO cell lines showed either no significant change, or showed a decrease in Qp compared to parent/control cultures.

Figure 3:
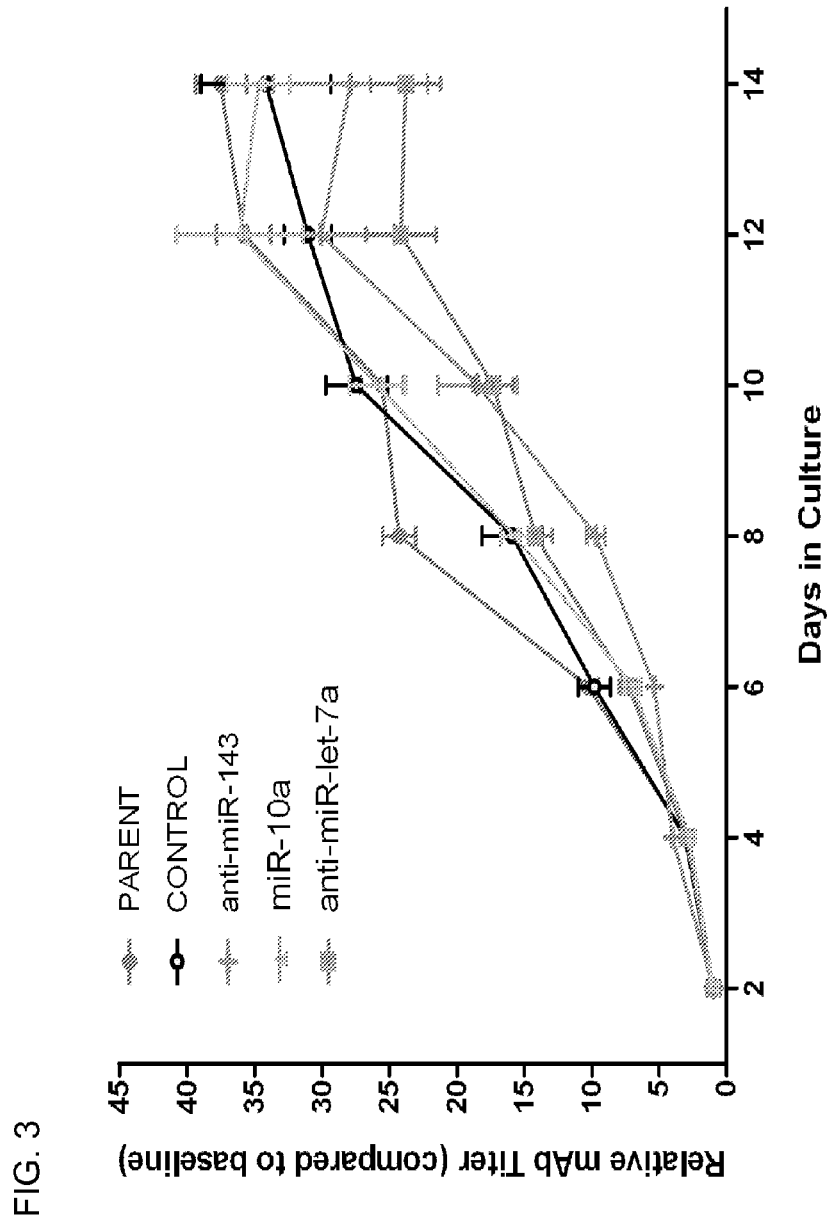
FIG. 3 is a graph showing recombinant antibody titer (relative to baseline levels measured at day 2) from anti-miR-let-7a, anti-miR-143 and miR-10a modified CHO cell lines measured every two days.
Figure 4:
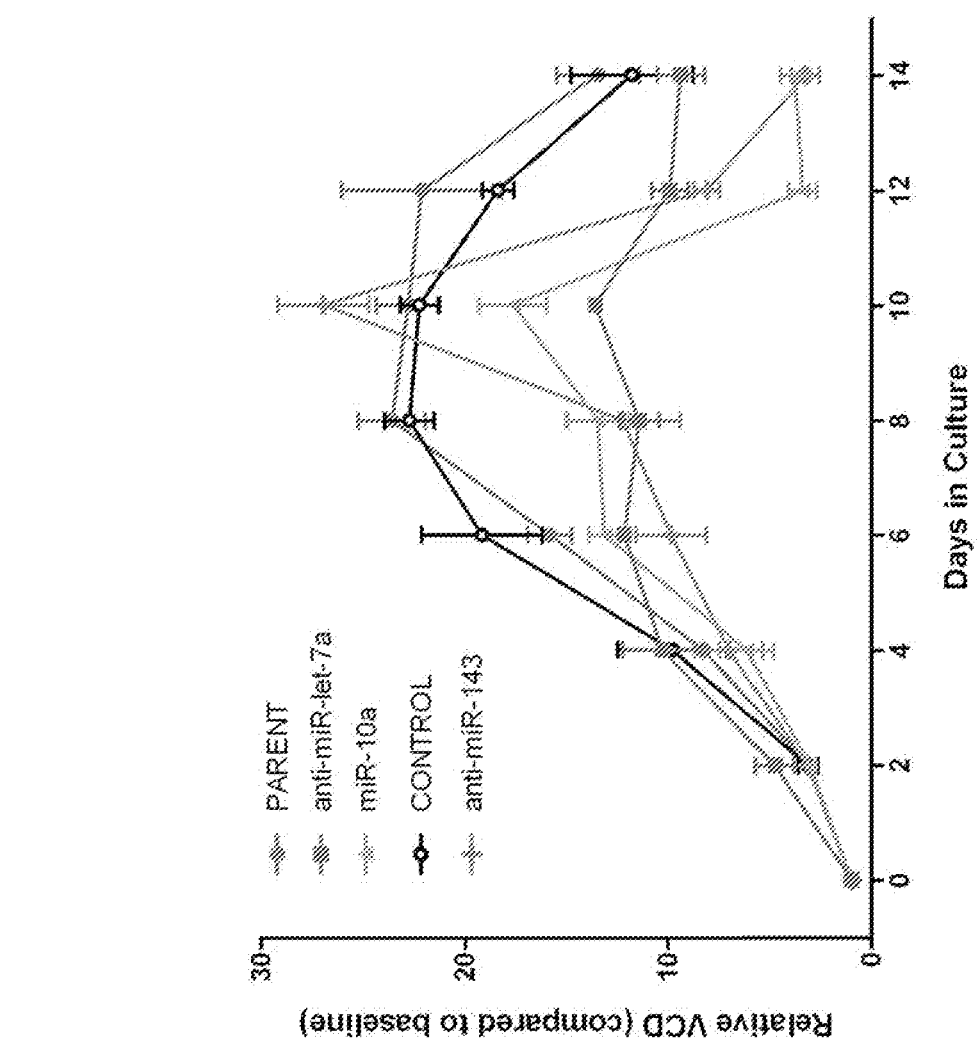
FIG. 4 is a graph showing VCD (relative to baseline levels measured at day 0) measured every two days in anti-miR-let-7a, anti-miR-143 and miR-10a modified CHO cell lines.

As recombinant polypeptide titer and VCD are the components of Qp, we investigated alterations in these parameters for each miR-modified cell line. Although miR-10a, anti-miR-143 and anti-miR-let-7a showed increased Qp compared to controls, the relative increase in their titer is similar to that observed in parent or control cell lines (FIG. 3). Additionally, modified CHO cells producing anti-miR-let-7a, reached a maximum VCD of only half of the parent or control lines (FIG. 4). MiR-10a and anti-miR-143 modified lines peaked in VCD at levels higher than those of anti-miR-let-7a at day 10 but their growth decreased substantially from day 12 to day 14, while anti-miR-let-7a remained at a relatively constant level through day 14. Growth at a reduced cell density may indicate a favorable redirection of cellular energy toward recombinant polypeptide synthesis rather than on proliferation of the culture (Browne and Al-Rubeai, (2009) Selection methods for high-producing mammalian cell lines. In: Al-Rubeai M, editor. *Cell Line Development*, Series: Cell Engineering 6, Springer Science+Business Media B.V. p. 127-151). Taken together, inhibition of miR-let-7a provided the greatest increase in Qp with the most prolonged growth profile of all miR-modified lines evaluated.

Inhibition was Consistent in an Additional mAb-Producing CHO Cell Line

Figure 5:
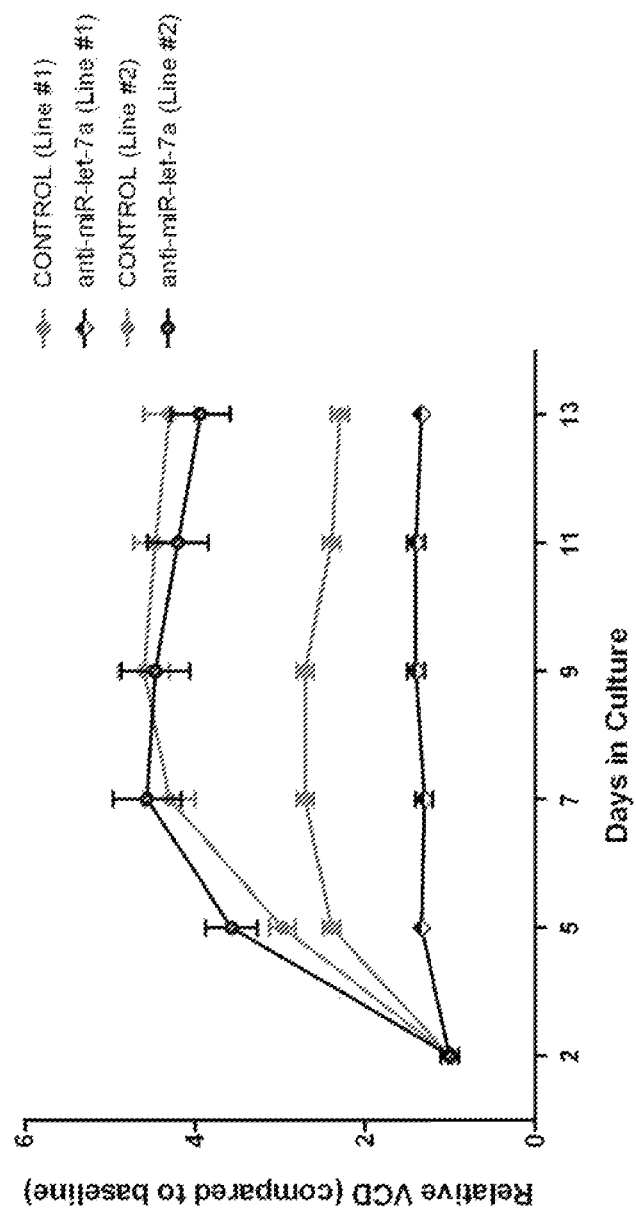
FIG. 5 is a graph showing relative VCD from two antibody-producing cell lines measured during fed batch assay of parental cultures transduced with anti-miR-let-7a lentivectors or vector controls. Results are shown as relative VCD levels compared to baseline (day 0).
Figure 6:
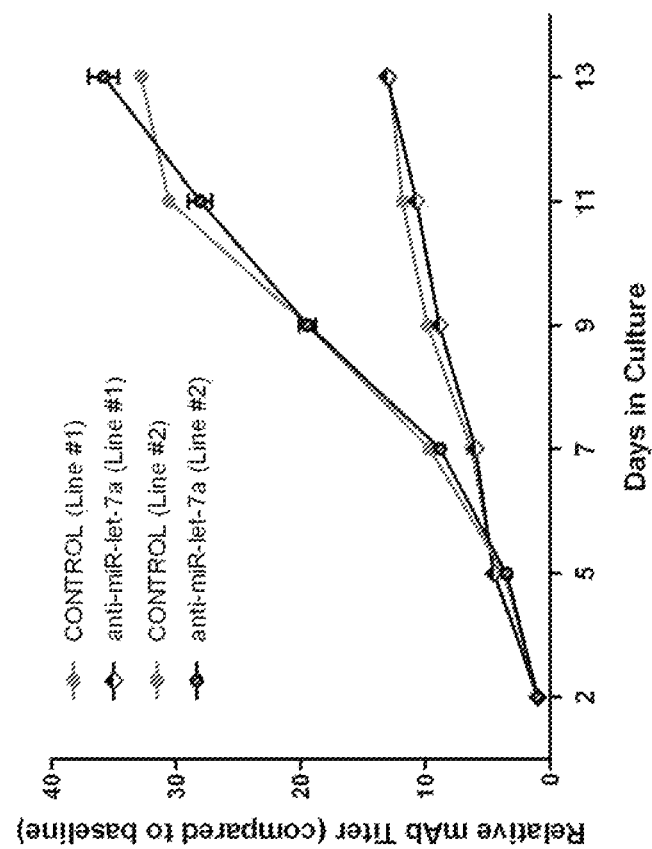
FIG. 6 is a graph showing recombinant antibody titers (relative to baseline measured at day 2) from anti-miR-let-7a-modified cultures and controls evaluated every two days.

To determine whether the effects of anti-miR-let-7a on CHO growth and productivity were specific to the initially tested producer cell line, or if this effect could be more generalized to other production cultures, an additional CHO cell line with a higher production capacity and producing a different mAb was selected. Results in the two mAb-producing cell lines tested were similar to each other in that anti-miR-let-7a cell lines maintained similar or reduced VCD over time with similar final mAb titer compared to control (FIGS. 5 and 6), leading to 50%, and 68% increases in Qp compared to control (FIG. 7). 2 µg purified antibody from miR or anti-miR-modified lines was reduced and assessed by reverse phase LC/MS for equivalence to parental lines in fidelity and integrity. Reverse phase LC/MS further verified that the mAb product from the anti-miR-modified cell lines was equivalent to parental lines in fidelity and integrity (FIGS. 12A and B). Interestingly, an inverse relationship was observed between the initial mAb production capabilities of the parental cell line and the percent increase in Qp upon introduction of anti-miR-let-7a (FIG. 7). Specifically the second cell line displayed a 1.6-fold increased production capacity compared to the first cell line, and this translated to a lower increase in Qp (approximately 1.4 fold), suggesting that miR modification may generally affect recombinant polypeptide production in a positive manner but may have a larger benefit to lower-producing cell lines.

Anti-miR-Let-7A Increased Targets Important for CHO Cell Productivity

To understand the functional effects of miR-let-7a inhibition, multiple predicted and validated targets of miR-let-7a were examined that have been shown in a myriad of cell types and disease settings to regulate multiple pathways including proliferation, stress resistance, and protein translation (De Vito et al., (2011) Let-7a is direct EWS-FLI-1 target implicated in Ewing's Sarcoma development. PLoS ONE 6(8):1-11, Sampson et al., (2007) MicroRNA Let-7a down-regulates MYC and reverts MYC-induced growth in Burkitt Lymphoma cells. Cancer Res 67(20):9762-9770; Johnson et al., (2005) RAS is regulated by the let-7 microRNA family. Cell 120:635-647; Mathonnet et al., (2007) MicroRNA inhibition of translation initiation in vitro by targeting the cap-binding complex eIF4F. Science 317 (5845):1764-7).

Since the specific effect of miR-let-7a in CHO cells has not been previously examined, we selected a panel of potential targets involved in pathways that could be of specific relevance to production culture. Within this panel of miR-let-7a-targets were three classes of targets that could be important for the mechanism of this miR on CHO cell productivity: (1) mRNAs previously shown to be modulated by mRNA degradation, including HMGA2, MYC, NF2, NIRF, RAB40C, PRDM1, and Integrin-b3; (2) mRNAs shown to be regulated by miR-let-7a translational inhibition, such as RAS, IGF, and EIF2A; and (3) mRNAs bioinformatically predicted to be miR-let-7a targets, such as EIF4A. (Muller (2008) MicroRNAs as targets for engineering of CHO cell factories. Trends in Biotechnology 26(7):359-365; De Vito et al., (2011) Let-7a is direct EWS-FLI-1 target implicated in Ewing's Sarcoma development. PLoS ONE 6(8):1-11; Sampson et al., (2007) MicroRNA Let-7a downregulates MYC and reverts MYC-induced growth in Burkitt Lymphoma cells. Cancer Res 67(20):9762-9770; Meng et al., (2007) The MicroRNA let-7a modulates interleukin-6-dependent STAT-3 survival signaling in malignant human cholangiocytes. Journal of Biological Chemistry 282(11): 8256-8264; Wang et al., (2012) NIRF is frequently upregulated in colorectal cancer and its oncogenicity can be suppressed by let-7a microRNA. Cancer Letters 314:223-231; Yang et al., (2011) Low-level expression of let-7a in gastric cancer and its involvement in tumorigenesis by targeting RAB40C. Carcinogenesis 32(5):713-722; Lin et al., (2011) Follicular dendritic cell-induced microRNA-mediated upregulation of PRDM1 and downregulation of BCL-6 in non-Hodgkin's B-cell lymphomas. Leukemia 25(1):145-152; Muller et al., (2008) MicroRNAs as targets for engineering of CHO cell factories. Trends in Biotechnology 26(7):359-365; Johnson et al., (2007) The let-7 microRNA represses cell proliferation pathways in human cells. Cancer Res 67:7713-7722; Lu et al., (2011) Hypermethylation of let-7a-3 in epithelial ovarian cancer is associated with low insulin-like growth factor-II expression and favorable prognosis. Cancer Res 67(21):10117-10122; and Mathonnet et al., (2007) MicroRNA inhibition of translation initiation in vitro by targeting the cap-binding complex eIF4F. Science 317(5845):1764-7).

Figure 8:
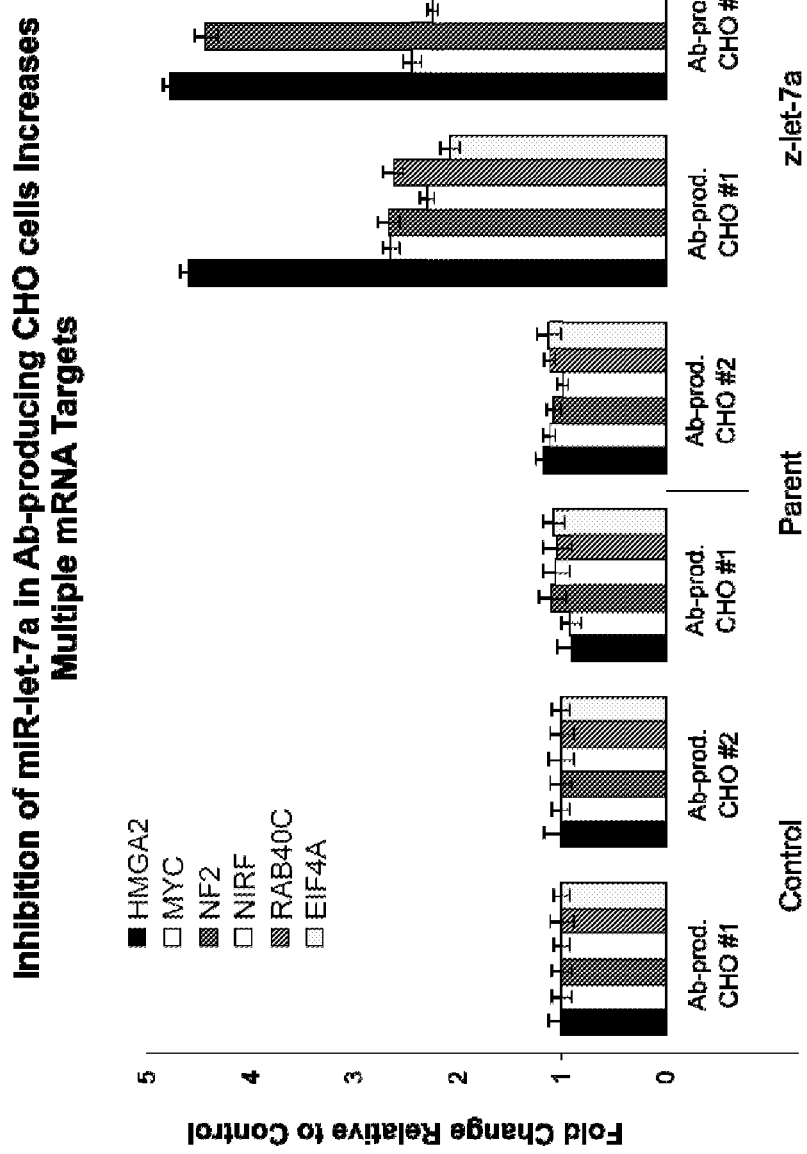
FIG. 8 is a graph showing fold changes in multiple mRNA targets in CHO producer cells evaluated by TaqMan quantitative PCR in miR or anti-miR-modified cell lines following inhibition of miR-let-7a as compared to control lines. Bars represent mean±SD.

Results indicated that inhibition of miR-let-7a in two different mAb-producing CHO cell lines led to increased mRNA levels of multiple miR-let-7a targets, including HMGA2, MYC, NF2, NIRF, RAB40C and EIF4A (FIG. 8). Other genes, such as PRDM1, Integrin-B3, IGF, RAS and EIF2A did not exhibit altered mRNA expression levels following inhibition of miR-let-7a (data not shown). In previous work, RAS has been shown to be inhibited translationally rather than through mRNA degradation; therefore, we measured RAS protein expression and found increased levels upon inhibition of miR-let-7a (FIG. 9). Key pathways affected by mRNA or protein alterations resulting from miR-let-7a inhibition in mAb-producing CHO cell lines include proliferation, apoptosis, resistance to stress, cellular metabolism, and regulation of the translational and/or secretory machinery (Muller et al., (2008) MicroRNAs as targets for engineering of CHO cell factories. Trends in Biotechnology 26(7):359-365; Barron et al., (2011) Engineering CHO cell growth and recombinant protein productivity by over expression of miR-7, Journal of Biotechnology 151(2):204-11; De Vito et al., (2011) Let-7a is direct EWS-FLI-1 target implicated in Ewing's Sarcoma development. PLoS ONE 6(8):1-11; Sampson et al., (2007) MicroRNA Let-7a down-regulates MYC and reverts MYC-induced growth in Burkitt Lymphoma cells. Cancer Res 67(20):9762-9770; Meng et al., (2007) The MicroRNA let-7a modulates interleukin-6-dependent STAT-3 survival signaling in malignant human cholangiocytes. Journal of Biological Chemistry 282(11):8256-8264; Wang et al., (2012) NIRF is frequently upregulated in colorectal cancer and its oncogenicity can be suppressed by let-7a microRNA. Cancer Letters 314:223-231; Yang et al., (2011) Low-level expression of let-7a in gastric cancer and its involvement in tumorigenesis by targeting RAB40C. Carcinogenesis 32(5):713-722). These pathways and the potential role of the targets of miR-let-7a in mediating these pathways are summarized in FIG. 10.

Our results show that inhibition of miR-let-7a in CHO cells led to changes in multiple genes/proteins previously associated with cell cycle control/proliferation and apoptosis, stress response, cellular metabolism, and protein transcription/translation. Specifically, our results indicated that miR-let-7a altered RAS, MYC, NF2, RAB40C, NIRF and HMGA2, which have been shown to regulate cell proliferation and apoptosis in systems other than CHO (FIG. 10). In addition to cell proliferation and apoptosis, MYC and RAS may influence the ability to adapt to stress and to overcome metabolic deficiencies, both of which are important for the proper processing of proteins and regulation of transcription factors (FIG. 10). eIF4a, which plays an important role in regulating translation initiation essential for cells with high protein synthesis rates, was also regulated by miR-let-7a.

C. CONCLUSION

Inhibition of miR-let-7a in multiple mAb-producing CHO cell lines used actively in production cell culture led to increased specific productivity and favorable growth characteristics through the regulation of multiple mRNA and protein targets in pathways important for recombinant polypeptide production. Taken together, results from this study indicate that modulation of one or more microRNAs may be an effective tool to increase production capabilities beyond their current limits.

TABLE 1 microRNAs selected for modulation in antibody-producing CHO cell lines.

| miRNA | Exemplary Rationales for Evaluation | Target Genes |
|---|---|---|
| miR-let-7a | Regulates cell proliferation, cell cycle progression and apoptosis. Regulates transcriptional initiation. Controls cell cycle to avoid replicative stress-induced senescence. | Ras, c-myc, HMGA2, E2F2, CCND2, NF2, CDK6 |
| miR-10a | Upregulates protein translation/synthesis Alters cell survival, apoptosis and self-renewal pathways | HOX genes, ribosomal proteins, TRAIL pathway |
| miR-16 | Regulates cell cycle progression, cell proliferation and apoptosis | BCL-2, CCND1, WT1 |
| miR-21 | Overexpressed in numerous cancers. Regulates apoptosis. Increases during cold stress/heat shock to facilitate adaptation to stress conditions and increased cell survival | Caspase 3, PDCD4, NFIB, TPM1, PTEN/AKT signaling |
| miR-101 | Regulates proliferation, histone methylation, and stem cell pluripotency | EZH2 |
| miR-145 | Downregulated in multiple cancers and in B cell malignancies. Regulates cell proliferation and apoptosis | Myc, IRS1, MAPK7, ERK5, FLI1, DFF45 |
| miR-143 | Downregulated in multiple cancer types. Regulates NFkB-dependent proliferation and apoptosis. Alters glucose/energy metabolism through ORP8 (AKT signaling) | ORP8, AKT signaling, MPAK7, ERK5 |

TABLE 2

PCR confirmation of miRNA expression in lentivector transduced cell lines. Levels of miR or anti-miR expression in miR-modified cell lines relative to a parental cell line were evaluated by TaqMan or QuantiMir RT PCR.

| miRNA | Fold Overexpression |
|---|---|
| Parent | 1 |
| anti-miR-let-7a | 1329 |
| miR-10a | 272 |
| anti-miR-10a | No primers available |
| anti-miR-16 | 1304 |
| miR-21 | 18 |
| anti-miR-21 | 683 |
| anti-miR-101 | No primers available |
| anti-miR-143 | 255 |
| anti-miR-145 | 65 |

TABLE 3

Relative VCD in all miR-modified Ab-producing CHO cell lines. Shown are the means ± SD of triplicate VCD values compared to each miR-modified or control cell line's baseline (day 0) value.

| Culture Day | PARENT | anti-miR-let-7a | miR-10a | anti-miR-16 | anti-miR-21 | miR-21 |
|---|---|---|---|---|---|---|
| 0 | 1.0 ± .00 | 1.0 ± .00 | 1.0 ± .00 | 1.0 ± .00 | 1.0 ± .00 | 1.0 ± .00 |
| 2 | 3.1 ± .32 | 4.8 ± .93 | 3.0 ± .12 | 3.2 ± .92 | 2.0 ± .37 | 5.5 ± .53 |
| 4 | 8.3 ± .29 | 10.3 ± 1.9 | 6.1 ± 1.3 | 7.9 ± .81 | 8.4 ± .59 | 16.5 ± 1.0 |
| 6 | 15.8 ± 1.1 | 12.2 ± .22 | 13.2 ± .76 | 15.1 ± 2.0 | 18.1 ± 1.9 | 20.0 ± 4.1 |
| 8 | 23.6 ± 1.6 | 11.4 ± .97 | 13.5 ± 1.6 | 15.6 ± 2.5 | 23.2 ± .56 | 24.6 ± 2.8 |
| 10 | 22.8 ± 1.5 | 13.6 ± .24 | 17.6 ± 1.7 | 12.7 ± 2.5 | 23.5 ± .92 | 11.9 ± 2.9 |
| 12 | 22.1 ± 3.9 | 9.9 ± .89 | 3.4 ± .71 | 11.0 ± 2.3 | 20.8 ± 1.6 | 7.8 ± 4.4 |
| 14 | 13.5 ± 2.0 | 9.4 ± 1.2 | 3.8 ± .74 | 8.5 ± 1.8 | 20.4 ± .83 | 6.0 ± .96 |

| Culture Day | CONTROL | anti-miR-10a | anti-miR-143 | anti-miR-101 | anti-miR-145 |
|---|---|---|---|---|---|
| 0 | 1.0 ± .00 | 1.0 ± .00 | 1.0 ± .00 | 1.0 ± .00 | 1.0 ± .00 |
| 2 | 3.1 ± .48 | 2.9 ± .95 | 3.2 ± .18 | 2.0 ± .03 | 1.5 ± .35 |
| 4 | 9.8 ± 2.6 | 10.2 ± 1.2 | 7.0 ± 1.7 | 7.4 ± 2.2 | 6.9 ± .48 |
| 6 | 19.2 ± 2.9 | 14.9 ± 2.5 | 9.9 ± 1.7 | 9.1 ± 2.9 | 19.3 ± 2.2 |
| 8 | 22.7 ± 1.2 | 16.7 ± 3.1 | 12.2 ± 2.8 | 12.6 ± 3.7 | 20.1 ± .81 |
| 10 | 22.3 ± .93 | 16.7 ± 2.9 | 27.0 ± 2.3 | 26.6 ± 6.0 | 21.4 ± 1.4 |
| 12 | 18.4 ± .77 | 3.3 ± .27 | 8.1 ± .63 | 14.5 ± 2.8 | 17.7 ± .65 |
| 14 | 11.8 ± 3.0 | 5.4 ± 1.1 | 3.3 ± .70 | 4.9 ± 5.5 | 16.2 ± .44 |

TABLE 4

Relative Titer in all miR-modified Ab-producing CHO cell lines. Shown are the means ± SD of triplicate titer values compared to each miR-modified or control cell line's baseline (day 2) value.

| Culture Day | PARENT | anti-miR-let-7a | miR-10a | anti-miR-16 | anti-miR-21 | miR-21 |
|---|---|---|---|---|---|---|
| 2 | 1.0 ± .04 | 1.0 ± .04 | 1.0 ± .04 | 1.0 ± .02 | 1.0 ± .10 | 1.0 ± .03 |
| 4 | 2.9 ± .12 | 2.9 ± .25 | 2.7 ± .10 | 2.7 ± .56 | 3.2 ± .26 | 3.2 ± .12 |
| 6 | 10.3 ± .75 | 7.3 ± .70 | 7.0 ± .60 | 12.0 ± 1.2 | 11.6 ± .83 | 9.7 ± .81 |
| 8 | 24.3 ± 1.2 | 14.3 ± 1.3 | 15.7 ± 1.0 | 11.6 ± 3.8 | 26.4 ± 1.5 | 15.9 ± .96 |
| 10 | 25.5 ± 1.6 | 17.3 ± 1.5 | 25.8 ± 2.0 | 19.9 ± 1.4 | 26.5 ± 1.5 | 14.3 ± .32 |
| 12 | 35.8 ± 2.0 | 24.2 ± 2.6 | 36.1 ± 4.7 | 26.8 ± 6.4 | 39.5 ± 2.8 | 15.2 ± 2.3 |
| 14 | 37.5 ± 1.9 | 23.8 ± 2.6 | 34.7 ± 2.3 | 26.3 ± 6.2 | 38.9 ± 3.7 | 13.4 ± 2.1 |

| Culture Day | CONTROL | anti-miR-10a | anti-miR-143 | anti-miR-101 | anti-miR-145 |
|---|---|---|---|---|---|
| 2 | 1.0 ± .01 | 1.0 ± .03 | 1.0 ± .08 | 1.0 ± .01 | 1.0 ± .01 |
| 4 | 3.1 ± .35 | 2.7 ± .29 | 4.1 ± .53 | 3.1 ± .24 | 3.1 ± .08 |
| 6 | 9.8 ± 1.2 | 3.2 ± .40 | 5.4 ± .36 | 4.4 ± .12 | 12.5 ± .95 |
| 8 | 15.9 ± 2.2 | 6.7 ± .20 | 9.7 ± .70 | 6.8 ± .93 | 19.7 ± 2.6 |
| 10 | 27.4 ± 2.3 | 13.4 ± .27 | 18.5 ± 2.9 | 12.6 ± 2.7 | 29.6 ± 3.4 |
| 12 | 31.0 ± 1.8 | 23.8 ± 1.4 | 30.1 ± 5.5 | 26.4 ± 6.8 | 32.1 ± 2.5 |
| 14 | 34.1 ± 4.8 | 24.0 ± 1.5 | 27.9 ± 5.7 | 32.8 ± 5.9 | 35.9 ± 2.2 |

What is claimed is:

1. A method of producing a recombinant polypeptide in a mammalian cell culture, the method comprising:
   (a) obtaining mammalian cells having reduced miRNA-let-7a activity;
   (b) culturing the mammalian cells to produce the recombinant polypeptide; and
   (c) recovering the protein
   wherein the miRNA-let-7a activity is reduced by a microRNA inhibitor.

2. The method of claim 1, wherein the microRNA inhibitor comprises an antisense oligonucleotide inhibitor of miRNA-let-7a.

3. The method of claim 2, wherein the oligonucleotide inhibitor is chemically modified to improve nuclease resistance, to increase resistance to miRNA-directed cleavage by RISC and/or to increase binding affinity.

4. The method of claim 1, wherein the mammalian cell culture comprises mammalian cells that are transfected with an expression vector encoding the antisense oligonucleotide inhibitor of miRNA-let-7a.

5. The method of claim 1, wherein the mammalian cell culture comprises mammalian cells that are stably transfected with an antisense oligonucleotide inhibitor of miRNA-let-7a.

6. The method of claim 1, wherein the mammalian cell culture comprises mammalian cells that are transiently transfected with an antisense oligonucleotide inhibitor of miRNA-let-7a.

7. The method of claim 1, wherein the mammalian cell culture comprises mammalian cells selected from: Chinese hamster ovary (CHO) cells, mouse myeloma (NS0), human embryonic kidney (HEK 293), baby hamster kidney (BHK) cells, Vero cells, HeLa cells, Madin-Darby Canine Kidney (MDCK) cells, CV1 monkey kidney cells, 3T3 cells, myeloma cell lines, PC12, WI38 cells, COS-7 lines of monkey kidney fibroblasts, and C127.

8. The method of claim 1, wherein the mammalian cells comprise Chinese hamster ovary cells.

9. A method of producing a recombinant polypeptide in a mammalian cell culture, the method comprising:
   (a) obtaining mammalian cells having reduced miRNA-let-7a activity;
   (b) culturing the mammalian cells to produce the recombinant polypeptide; and
   (c) recovering the protein
   wherein the mammalian cells having reduced miRNA-let-7a activity comprise miRNA-let-7a genetic knockouts.

10. The method of claim 1, wherein the recombinant polypeptide is selected from the group consisting of an antibody or binding fragment thereof, a non-antibody protein, a fusion protein, a receptor, a ligand of a cell surface protein, a receptor, a secreted protein, and an enzyme.

11. The method of claim 10, wherein the antibody or binding fragment thereof is selected from multispecific antibodies, fully human antibodies, humanized antibodies, camelised antibodies, chimeric antibodies, CDR-grafted antibodies, single-chain Fvs (scFv), disulfide-linked Fvs (sdFv), Fab fragments, F(ab') fragments, and anti-idiotypic (anti-Id) antibodies.

12. The method of claim 1, wherein the cell culture has a specific productivity that is increased at least about 25% compared to a control cell culture that does not have reduced miRNA-let-7a activity.

13. The method of claim 1, wherein the cell culture has a maximum productivity determined at peak viable cell density (VCD) that is increased at least about 25% when compared to a control cell culture that does not have reduced miRNA-let-7a activity.

14. The method of claim 1, wherein the cell culture has an increased specific productivity when compared to a control mammalian cell culture that does not have reduced miRNA-let-7a activity.

15. The method of claim 1, wherein specific productivity of the cell culture has increased by at least 10%, 15%, 20%, 25%, 30%, 35%, 40%, 45%, 50%, 55%, 60%, 65%, 70% or 75%.

16. The method of claim 1, wherein the cell culture has a relative viable cell density of between about 1% and about 30% compared to a control cell culture that does not have reduced miRNA-let-7a activity.

17. A cell culture medium for producing a recombinant polypeptide in a mammalian cell comprising: a miRNA-let-7a microRNA inhibitor and a buffer, salt, carbohydrate, amino acid, vitamin, and trace essential element.

18. A recombinant polypeptide produced from a mammalian cell culture comprising mammalian cells transfected with an antisense microRNA inhibitor of miRNA-let-7a.

19. The cell culture medium of claim 17, wherein the microRNA inhibitor is an antisense inhibitor of miRNA-let-7a.

20. A host cell having reduced miRNA-let-7a activity capable of producing a recombinant polypeptide comprising a vector encoding the recombinant polypeptide and wherein the miRNA-let-7a activity is reduced by a microRNA inhibitor.

* * * * *